(12) United States Patent
Watkins, Jr. et al.

(10) Patent No.: US 7,612,325 B1
(45) Date of Patent: Nov. 3, 2009

(54) ELECTRICAL SENSOR FOR MONITORING DEGRADATION OF PRODUCTS FROM ENVIRONMENTAL STRESSORS

(76) Inventors: Kenneth S. Watkins, Jr., 372 River Dr., Dahlonega, GA (US) 30533; Shelby J. Morris, 35 Curte Rd., Hampton, VA (US) 23669

(\*) Notice: Subject to any disclaimer, the term of this patent is extended or adjusted under 35 U.S.C. 154(b) by 54 days.

(21) Appl. No.: 11/894,903

(22) Filed: Aug. 22, 2007

(51) Int. Cl.
*H01J 40/14* (2006.01)
*G06M 7/00* (2006.01)

(52) U.S. Cl. .................... 250/222.2; 250/221

(58) Field of Classification Search .......... 250/222.2, 250/221; 73/865.9, 866, 786, 802; 324/543, 324/544, 693, 541, 555, 71.1, 691; 374/5, 374/6; 422/533
See application file for complete search history.

(56) References Cited

U.S. PATENT DOCUMENTS

| 3,603,142 | A | * | 9/1971 | Saylak et al. ............... 73/776 |
| 4,675,662 | A | | 6/1987 | Kondo et al. |
| 6,276,214 | B1 | * | 8/2001 | Kimura et al. .............. 73/795 |
| 2007/0166831 | A1 | | 7/2007 | Watkins, Jr. et al. |

FOREIGN PATENT DOCUMENTS

| JP | 361044339 A | 3/1986 |
| JP | 2000356660 | 12/2000 |
| WO | WO 03/076953 | 9/2003 |
| WO | WO 2005/081930 | 9/2005 |

OTHER PUBLICATIONS

"An Electrical Approach to Monitor Wire and Cable Thermal Oxidation Aging Condition Bas4ed on Carbon Black Filled Conductive Polymer Composite", YangYang Sun et al., Journal of Polymer Science Jul 15, 2004.

\* cited by examiner

*Primary Examiner*—Que T Le
*Assistant Examiner*—Pascal M Bui-Pho
(74) *Attorney, Agent, or Firm*—Kenneth S. Watkins, Jr.

(57) ABSTRACT

An environmental degradation sensor for environmentally sensitive products such as food, pharmaceuticals or cosmetic products provides the degraded state and estimated remaining life of the product. The sensor is made of a polymeric matrix and conductive filler. A control agent, selected to adjust a reaction rate of the sensor to environmental conditions, allows correlation of an electrical property of the sensor to a degraded state of the product. The sensor may be integrated with a passive RFID to provide product identification and degradation status wirelessly via reader. The sensor improves product safety, reduces cost of premature product disposal and, combined with RFIDs, improves the security of products through combined product degradation monitoring and tracking.

22 Claims, 16 Drawing Sheets

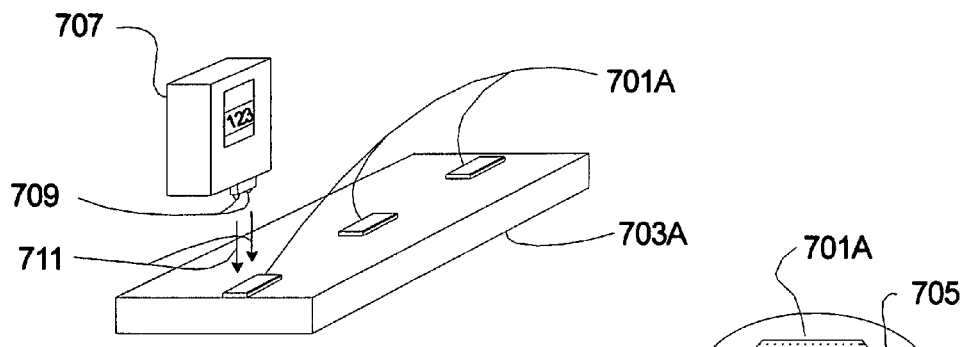
FIG. 7A
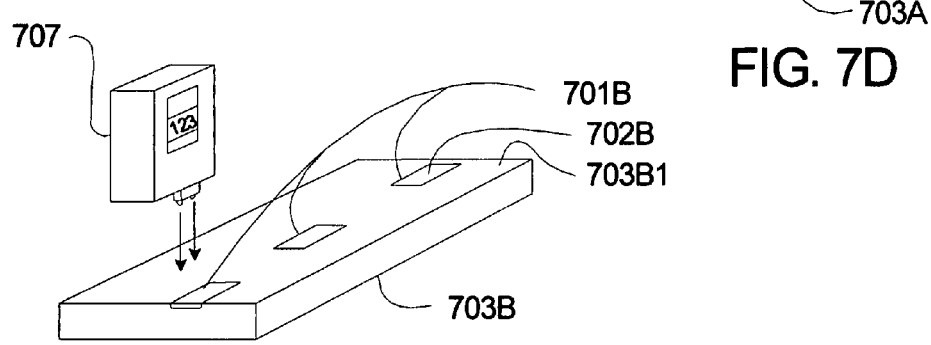
FIG. 7B
FIG. 7D
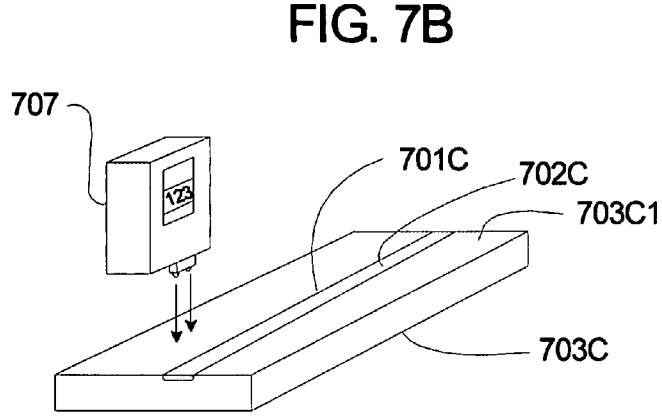
FIG. 7C

ELECTRICAL SENSOR FOR MONITORING DEGRADATION OF PRODUCTS FROM ENVIRONMENTAL STRESSORS

CROSS REFERENCE TO RELATED APPLICATIONS

This application claims the benefits of PCT Application No. PCT/US2006/006187 filed 22 Feb. 2006 claiming benefit of U.S. Provisional Application No. 60/655,379 filed Feb. 23, 2005.

FIELD OF THE INVENTION

The present invention relates to environmental degradation sensors and, more particularly, to degradation sensors for environmentally sensitive products. The present invention also relates to apparatus and methods for sensor construction, sensor applications, remaining life prediction, and methods of product degradation tracking and networking.

BACKGROUND OF THE INVENTION

A great many products used by consumers, businesses and organizations degrade rapidly unless stored in controlled environments. These products include food, pharmaceutical and chemical products. All polymeric products and many non-polymeric products are subject to aging effects to varying degrees, and often under multiple complex degradation mechanisms. Prematurely degraded products may pose health and safety risks to customers. Products properly stored may be disposed of prematurely due to conservative shelf-life dating.

A number of methods and sensors have been developed to indicate the degraded state and/or the remaining useful life such as product expiration dates and in-situ degradation sensors.

Expiration dates have been used for some time and provide a low-cost and user-friendly interface. However, expiration date methods assume environmental specification conformance within predetermined ranges and provide no feedback or date correction should the actual environmental conditions be exceeded. Product manufacturers must compensate for unknown environmental exposure by conservative product expiration dating; wasting product life, which could otherwise be used if the actual environmental exposure is known. On the other hand, consumption of spoiled food or drugs that have lost their efficacy poses serious health risks and associated costs. Many materials such as solid propellants used in aerospace applications may degrade quickly in extreme environments, making shelf life dating unsuitable.

Another type of degradation sensor used for determining degradation of products is the time-temperature integrator (TTI). TTIs may take the form of analog devices such as degradation sensors utilizing chemical reactions resulting in color changes. The color changes correspond to an integrated time-temperature condition of the product or package and provide a more flexible method to indicate product expiration as compared to date stamping. However, these devices are difficult to vary the response for different degradation models and are of limited use where direct observation of the sensor is difficult. In addition, color change indicators are difficult to use with automated or degradation communications systems.

Another approach for determining remaining product life is the digital time-temperature integrators. These devices utilize a temperature sensor such as a thermocouple or thermistor and a digital clock. Time and temperature are logged at predetermined time intervals and stored in a memory. A microprocessor, either co-located with the data logger or separate from the datalogger, integrates the time-temperature data in an algorithm modeling the degradation factors of the product. These devices offer great flexibility of degradation modeling since virtually any degradation mechanism may be modeled by a microprocessor once the necessary time and temperature data has been collected. However, these devices suffer the disadvantage of requiring power for the data logging and timing functions, and microprocessor power if integrated in the device. Power requirements prevent practical use of these devices in many automated or wireless system applications such as passive RFID tags. The complexity of the devices also makes integration in individual product packaging difficult and the cost is relatively high.

An improved method is needed to monitor the condition of degradable products that overcomes the drawbacks of current methods.

OBJECTS AND SUMMARY OF THE INVENTION

Therefore, an object of the present invention is to provide an environmental degradation sensor and method for monitoring the condition of degradable products that addresses the shortcomings of previous methods.

Another object of the present invention is to provide a degradation sensor that integrates aging effects due to changing environmental conditions continuously and without electrical power except when the sensor is interrogated.

Another object of the present invention is to provide a degradation sensor that models the degradation mechanisms of the product it is monitoring without complex computational power.

Another object of the present invention is to provide a degradation sensor that can be modified to provide degradation modeling for polymeric, non-polymeric and composite products.

Another object of the present invention is to provide a degradation sensor that can be modified by addition of control agents to model a wide variety of product degradation mechanisms.

Another object of the present invention is to provide a degradation sensor in which the response can be modeled to provide estimated remaining life based on assumed conditions.

Another object of the present invention is to provide a degradation sensor that is small and low in cost.

Another object of the present invention is to provide a degradation sensor that can be integrated into the product through known product manufacturing methods such as casting, molding, and extrusion.

Another object of the present invention is to provide wired and wireless methods of communicating degradation sensor data.

Another object of the present invention is to provide a method of integrating a degradation sensor in radio frequency identification devices.

Still another object of the present invention is to provide a method of communicating product degradation sensor data to a network accessible by product manufacturers, product distributors and product users.

Yet another object of the present invention is to provide a method of communicating product identification and degradation data to a network accessible by product manufacturers, product distributors and product users.

The method of the present invention makes use of a conductive composite degradation sensor for products which degrade from environmental stressors such as temperature, humidity, and ionizing radiation. The degradation sensor comprises a polymeric matrix and a conductive filler. In some embodiments a control agent is added which modifies the environmental stress response of the sensor. The conductive filler provides a sensitive means to indicate the time-dependent shrinkage of the conductive composite by measuring the resistance of the sensor. The resistance of the sensor can be correlated with resistivity-stressor-time data to provide product degradation status and, with additional environmental stressor input, allows prediction of remaining product life.

The control agent is a component of the conductive composite which modifies an environmental stress response, such as time-temperature-dependent shrinkage of the conductive composite resulting in a resistivity vs. time response which changes with product degradation in a predictable manner. In the preferred embodiments the resistivity vs. time response is a resistivity decrease as the conductive composite shrinks with time in an environmental stressor condition. These embodiments provide good correlation with product degradation since many of the degradation mechanisms of the sensor elements (such as chain scission, chain crosslinking and mass loss) results in volumetric shrinkage of the product and the sensor element.

Two primary approaches are used to model sensor resistivity response with degradation of the product to be monitored. The first approach selects at least one of the polymeric components of the product as a polymeric component of the matrix of the sensor. Assuming the conductive filler is inert with respect to other sensor components and degradation mechanisms involved, the degradation mechanisms of the polymeric component of the sensor are the same as those of the polymeric component of the product. Since several of the dominant degradation mechanisms for polymers (cross-linking, chain scission and loss of volatile fractions) result in volumetric shrinkage of the polymeric component, the resistivity of the sensor will decrease as the polymeric component of the product degrades. Since multiple environmental stressors often result in similar degradation mechanisms, the sensor can respond to one or more environmental stressors.

By measuring the resistivity-time response of the sensor under controlled environmental conditions and comparing measurements of a selected degradation measurement (such as hardness, elongation, or other mechanical, chemical or sensory degradation measurements) of the product, sensor response and product degradation state may be modeled and equated by graphical, numerical or statistical methods. Data collected at multiple temperatures (or other environmental stress conditions) may be used to predict remaining life by measuring resistivity data through use of Arrhenius methodology. An advantage of this approach is that the sensor can be made simply by adding a conductive filler to the product material. This approach is especially useful when integrating the sensor into the product, such as integrated degradation sensors in wire and cable insulation, composite structures and polymeric building materials such as building siding and decking. This approach is also useful for products having complex degradation mechanisms such as those of food products.

A second approach for modeling product degradation is to select a polymeric component of the sensor and one or more control agents independent of the product material, but so that the resistivity response of the sensor can be correlated to a selected degradation measurement of the product under environmental stressor conditions. The actual degradation mechanisms of the conductive composite sensor may or may not be the same as the degradation mechanisms of the product. The flexibility of this approach is especially useful in designing a sensor to detect degradation of non-polymeric products, or products which degrade quickly such as food or some pharmaceutical products. This approach also allows modeling and monitoring products whose degradation mechanisms are somewhat different from those of polymeric sensors.

In the second approach, the degradation of the product is modeled by selecting a degradation measurement and measuring the degradation under controlled environmental conditions. The degradation measurement includes mechanical or physical measurements such as hardness, elongation, density, mass loss or fatigue strength; chemical measurements such as molecular weight or crystallinity; sensory measurements such as smell, color or taste; and biological measurements such as bacteria counts. The sensor conductive composite components (polymer and control agent) are selected to provide resistivity-time response, which may be modeled to the selected degradation response of the product. A control agent may be any sensor component which modifies the sensor response to environmental sensors in a manner allowing correlation with the product degradation. It may be a chemical component of the sensor element itself, or it may be a physical alteration of the sensor element or sensor package which provides the desired resistivity-time response under tested environmental conditions.

The sensor conductive composite components may be selected so that the resistivity-time response from the dominant shrinkage mechanisms of the sensor can be correlated to the degradation of the product degradation. For example, curing of two-part epoxy systems or mass loss of volatile components of a conductive composite may be advantageous for short lived products which degrade quickly with temperature such as food products. Although the actual degradation mechanisms may differ, the conductive components and control agents may be selected so that the resistivity response of the sensor can be correlated to the desired degradation measurement used for the product.

In a preferred embodiment of the invention, the product degradation measurements are made at multiple temperatures and, in cases where the response follows Arrhenius behavior, a conductive composite system can be selected to model the activation energy and decay constants of the product degradation to provide sensor-product correlation over a range of temperatures. Such modeling also allows prediction of remaining life based on resistivity measurement of the sensor and using assumed environmental conditions.

The sensors of this invention may be used for a wide variety of environmental stressors, including temperature, humidity, radiation, and chemical vapors or suspensions. Where the sensor utilizes a polymeric component of the product, the degradation of the sensor will "automatically" follow that of the product. Since many of the degradation mechanisms of polymers (including chain scission and cross linking) are affected by radiation and other environmental conditions as well as temperature, the degradation of these other environmental conditions is also integrated into the total degradation of the product. In cases where the degradation sensor utilizes conductive composites "designed" to model degradation effects of the product, the predominant environmental degradation mechanism of the product may be used to select the sensor components. In other embodiments, multiple sensor components may be used to model complex product degradation mechanisms or those that model multiple environmental stressor conditions.

The conductive composite selected for the sensor may be formed into a discrete sensor by connecting two electrodes to a sensor element for measurement of sensor resistance. Discrete sensors may be physically attached or otherwise associated with the product, or disposed inside or outside product packaging. Placing the sensor inside product packaging ensures that the sensor is exposed to a similar environment as the product. In other embodiments, the sensor(s) are distributed into the product or packaging itself, for example, by extrusion, casting or molding processes.

Sensor communication may include contact reading, wired or wireless communication. Contact reading can be made with a resistance measuring instrument such as an ohmmeter having electrodes which contact a surface of the sensor element. The resistance can be converted to resistivity by incorporating the geometrical dimensions of the sensor and the electrode configuration and spacing on the reader. Wired communication utilizes a permanent, portable or temporary connector and conductor connecting the sensor to a resistance measuring instrument. Wireless communication may utilize passive or active transmitters or transponders and may utilize various modulation techniques known in the art to communicate sensor resistance measurements. In still other embodiments, threshold detectors may be incorporated into the transmitter so that simple binary communication provides a "go, no-go" communication of product status.

The resistance measuring instrument may incorporate degradation modeling algorithms for converting resistance readings to product degradation status, or remaining life of the product. Such modeling may be as simple as calibrating the face of an analog device to indicate product condition, or it may utilize microprocessors to indicate multiple degradation status conditions for multiple sensors and product types, as well as remaining life prediction capability.

The ability of the degradation sensor of this invention to inherently integrate degradation effects due to changing and multiple environmental conditions without electrical power makes the sensor especially compatible with radio frequency identification devices (RFIDs). Since electrical power is required only when the sensor is interrogated (sensor resistance being read), it is especially useful with passive RFIDs that can provide the interrogation power (applied voltage across the sensor) from the reader during RFID interrogation. In other embodiments, other wireless communications is used such as active radio frequency devices, laser, infra-red, optical, microwave and sonic devices may used.

Wired and wireless networks include multiple product entities such as product manufacturers (including multiple manufacturing entities for a product), product packaging entities, product distribution entities, product wholesaling and retail entities, and product end users. Any or all of the entities may include capabilities of reading, storing and transmitting sensor resistance and degradation data anywhere along the lifecycle of the product. The network utilizes sensor output and degradation status information stored by one or more network user entities, or by a network administrator.

BRIEF DESCRIPTION OF THE DRAWINGS

These and other features, aspects and advantages of the present invention will become better understood with regard to the following description, appended claims and accompanying drawings where:

FIG. 7A is a perspective drawing showing electrical contact measurement of composite degradation sensors distributed on a degradable product as separate sensors;

FIG. 7B is a perspective drawing showing electrical contact measurement of composite degradation sensors embedded in a degradable product with a surface of the sensors on an outside surface of the product;

FIG. 7C is a perspective drawing showing electrical contact measurement of composite degradation sensor distributed as a extended strip over the length of a degradable product;

FIG. 7D is a detail cross section showing an alternative embodiment utilizing an adhesive element such as an adhesive strip to provide adhesion of the degradation sensors or FIG. 7A to the product;

DESCRIPTION OF THE PREFERRED EMBODIMENTS

The following is a description of the preferred embodiments of a degradation sensor for temperature and other environmentally sensitive products that requires no electrical power until the sensor is interrogated.

Figure 1:
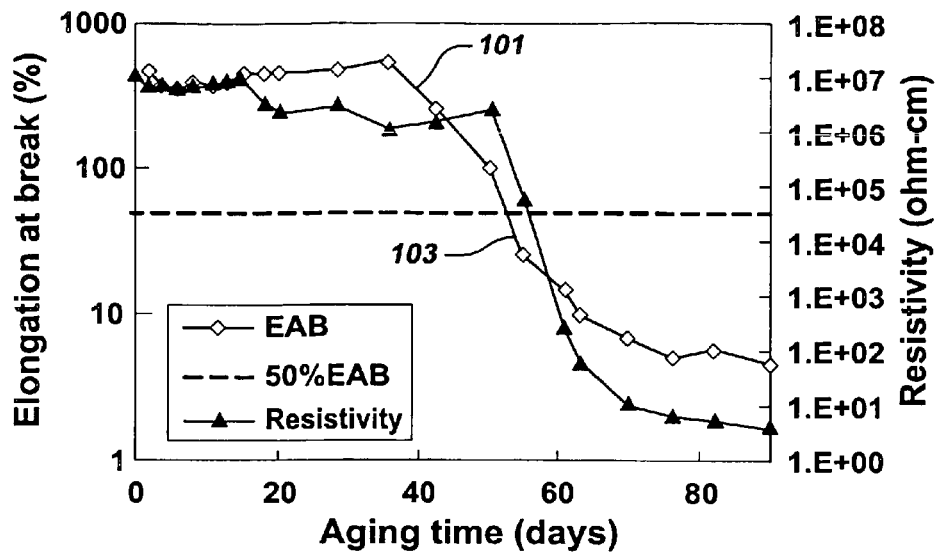
FIG. 1 is a plot showing correlation of resistivity and elongation at break of a composite degradation sensor made of an EPR matrix and a carbon black conductive filler aged in a convection oven at 130 degrees centigrade.

Prior work disclosing use of conductive composites to model aging of polymeric materials is disclosed in U.S. application Ser. Nos. 10/506,518 and 11/510,875, and PCT/US05/05609 hereby incorporated by reference. These references show a general decrease in resistivity of a conductive composite made of a polymeric matrix and conductive particle filler as the composite degrades. This is due to various degradation mechanisms such as mass loss, chain cross linking, and chain scission of the polymer matrix, resulting in a higher volume fraction of conductive particles as the polymer degrades. FIG. 1 shows a decrease in resistivity 101 of a composite degradation sensor made of ethylene propylene rubber (EPR) matrix and a carbon black conductive filler. As shown in the figure, resistivity drop during accelerated thermal aging (convective oven, 130 degrees centigrade) correlates to a loss of elongation-at-break 103 of the sensor's composite matrix during aging.

Several strategies can be used to model conductive composite electrical changes with degradation of a product under various environmental stress conditions such as temperature, humidity, and radiation. One such approach employs utilizing a polymer of the product being monitored as the matrix of the sensor. Assuming that the conductive particles are chosen to be inert with respect to the degradation mechanisms of the polymer of interest, and that a sensor made utilizing the polymeric component as a matrix is in the same environment as the product, degradation of the polymeric component of the sensor will be similar to that of the product. Resistivity of the sensor can be correlated to mechanical or chemical degradation measurements made of the polymer of interest during natural or accelerated aging and correlated by modeling such as graphical, numerical, statistical or Arrhenius modeling. Correlating sensor resistivity with product degradation may be used even when addition of conductive fillers (or additional components) results in sensor degradation response different from the polymeric component alone.

Such correlations of sensor resistivity and degradation properties of the polymer of interest allow a simple electrical measurement, resistance of a sensor (converted to sensor resistivity), to correlate to the mechanical or chemical condition of the product. Other electrical measurements may include conductivity, inductance, capacitance or impedance. Arrhenius methodology may be used to predict remaining life of the product for assumed environmental conditions. The advantage of such a strategy is that the sensor response is inherently similar to that of the product in virtually any environment since the "active" portion of the sensor is the polymeric component of the product.

A second approach is to "design" a conductive composite degradation sensor (conductive composite) whose resistivity can be correlated to degradation of any product for chosen environmental stress conditions. For example, the degradation of a polymeric or non-polymeric product may be tested under a thermal stress by measuring a degradation parameter such as a mechanical degradation measurement, a chemical degradation measurement, a biological degradation measurement or other degradation parameters such as color or smell under several temperature environments.

The components of a conductive composite sensor may be selected to provide a response that can be correlated with the degradation parameter or measurement of the product. The conductive composite sensor components chosen may degrade under one or more degradation mechanisms such as mass loss, chain scission, or chain cross linking, and modified by addition of reaction modifiers such as reaction catalysts, environmental filters or barriers. Or, mixtures of several degradation components may be combined in order to model the desired degradation parameter of the product. An advantage of this approach is that any product which degrades under an environmental stress may be "modeled" by a conductive composite sensor.

Example 1

Figure 2:
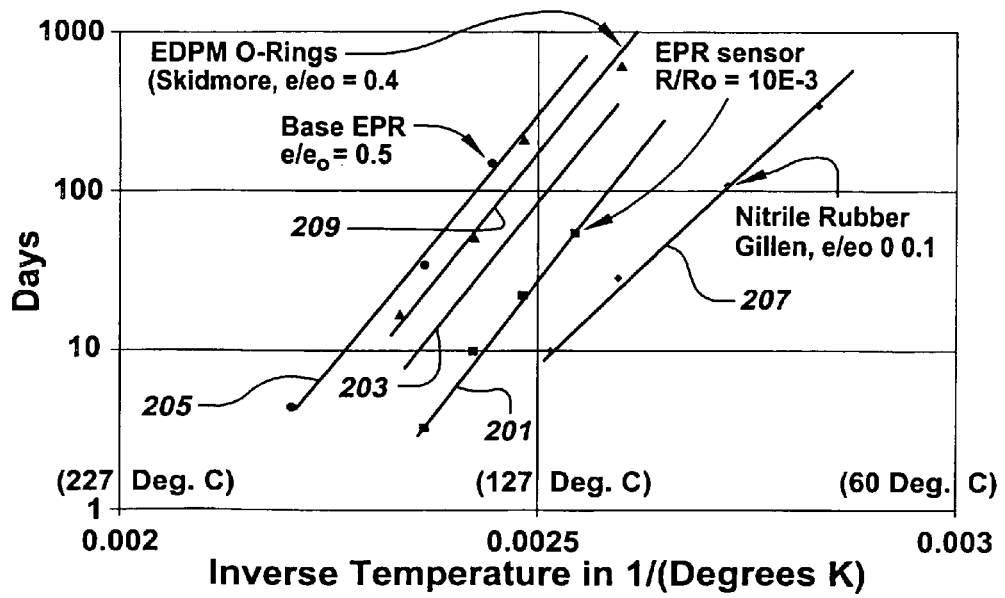
FIG. 2 is an Arrhenius diagram showing correlation of a conductive composite degradation sensor made by compounding EPR and carbon black with mechanical degradation of EPR insulation.

FIG. 2 is an Arrhenius diagram showing correlation of a conductive composite degradation sensor 201 made by compounding ethylene propylene rubber (EPR) and carbon black. The carbon black loading was adjusted to provide an initial resistivity of approximately 1E+8 ohm-cm. Another sensor 203 was made by adding a commercial anti-oxidant. The samples were aged in a thermo-oxidative environment (convective oven) at several temperatures and plotted on the Arrhenius diagram. The times plotted for the degradation sensors corresponded to a relative decrease in resistivity (3 decade decrease from the initial resistivity). A plot of the same EPR base material 205 as used in the degradation sensor, but plotted conventionally by mechanical degradation (50% drop in elongation), is shown for comparison. Activation energies of the two sensors (with and without anti-oxidant measured by resistivity decrease) and the EPR base polymer (measured by loss of elongation) are similar and shown for comparison. The degradation of different commercial materials (Nitrile rubber, Gillen et al. 207 and EDPR, Skidmore 209), are also shown for comparison.

The data indicates that the EPR sensors' resistivity drop results in approximately the same activation energy as that obtained by mechanical measurements of EPR degradation (loss of elongation). That data also shows that the time constant (Y-intercept) of the sensor can be adjusted by addition of anti-oxidant.

Example 2

Figure 3:
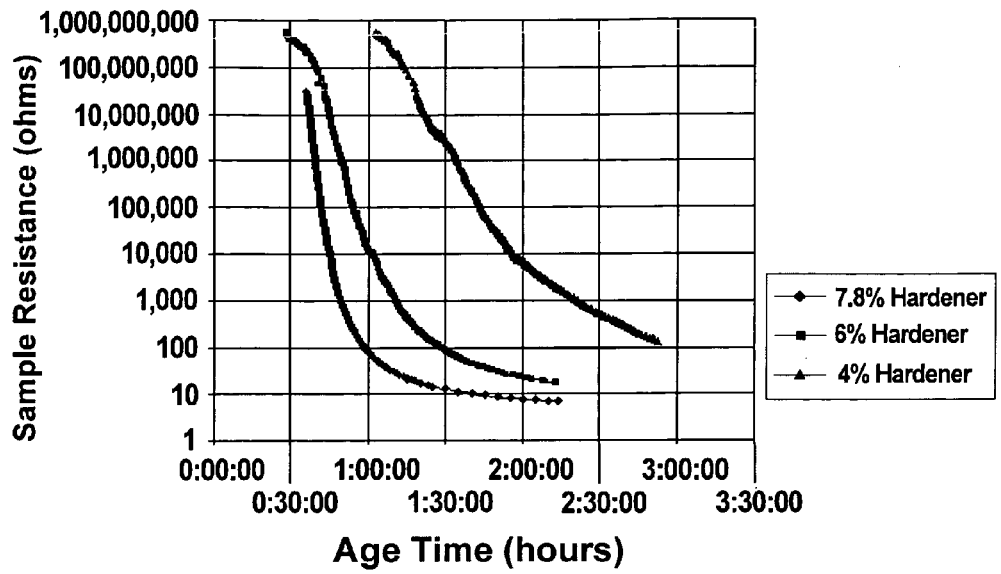
FIG. 3 is a resistivity vs. time chart for a degradation sensor made of a two-part epoxy (at several hardener/resin mixtures) thermoset material and a nickel conductive filler, aged at 60° C.
Figure 4:
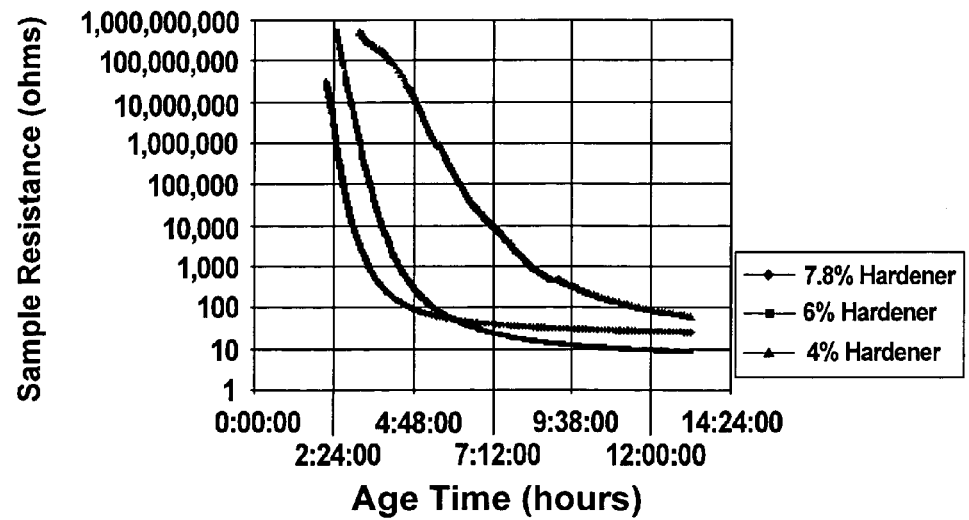
FIG. 4 is a resistivity vs. time chart for a degradation sensor made of the two-part epoxy thermoset material and a nickel conductive filler, aged at 40° C.

FIG. 3 is a resistivity vs. time chart for a degradation sensor made of a two-part epoxy (at several hardener/resin mixtures) thermoset material and a nickel conductive filler, aged at 60° C. FIG. 4 is a resistivity vs. time chart for a degradation sensor made of the two-part epoxy thermoset material and a nickel conductive filler, aged at 40° C. As the chemical crosslinking proceeds, volumetric shrinkage of the polymeric matrix increases the volume fraction of the conductive filler, causing the resistivity to decrease. Both trials utilized three specimens with different resin/hardener ratios. As seen from the charts, increasing hardener (control agent) percentage increases the rate of resistivity decrease, corresponding to an increased reaction rate (curing) of the epoxy. Increased temperature (environmental stressor) also increases the reaction rate, increasing the rate of decrease of resistivity and reducing the curing time of the epoxy.

Example 3

Figure 5:
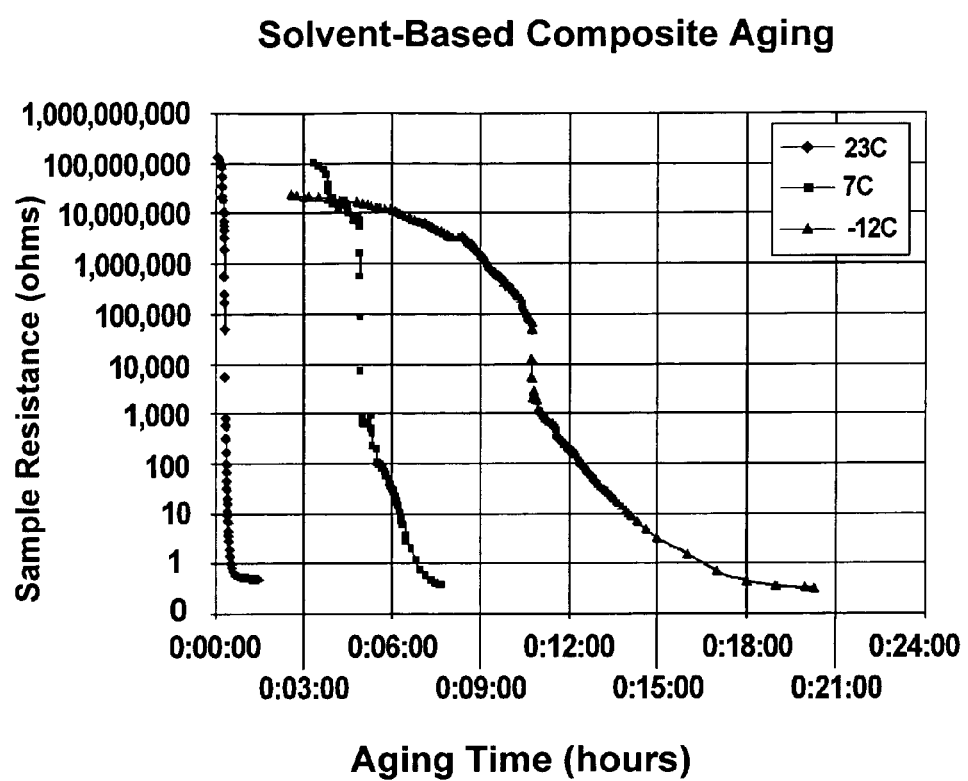
FIG. 5 is a resistivity-time chart of a conductive composite sensor made utilizing a volatile polymeric component and silver particles.

FIG. 5 is a resistivity-time chart of a conductive composite sensor made utilizing a volatile polymeric component and silver particles. The composite utilized in this test is a commercially available conductive pen product (Chemtronics CT-CW2200STP). As can be seen from the figure, the reaction rate of resistivity decrease increases with temperature (environmental stressor).

Selecting the matrix polymer for a degradation sensor can be used to determine the overall activation energy of the sensor reaction. Selection of a rate-affecting component such as the type and amount of an anti-oxidant in an elastomer or thermoplastic, can be used to adjust the time constant (Y intercept of the Arrhenius curve) of the reaction. Or, the resin and hardeners types may be selected in thermoset polymer matrixes to provide a desired activation energy and the resin/hardener ratios selected to control the time constant of the reaction.

Still another method of "designing" a degradation sensor so that the resistivity change of the conductive composite models the degradation of a desired product is to correlate product degradation with a composite comprising a volatile agent and a conductive filler such as that used in FIG. 5. The type of volatile agent (control agent) used in the conductive composite provides a means to select a reaction rate (in this case the mass loss of the volatile agent) in a temperature stress environment that correlates to a decrease in resistivity of the sensor with the degradation of the selected product. The reaction rate may be modeled not only by the type of volatile agent, but it may be modified by a reaction control agent such as a matrix or sensor package barrier or filter which affects the diffusion constants of the reaction to provide the desired modeling.

In the preferred embodiments, the resistivity of the sensor and degradation criteria (mechanical, chemical, or other) of the product are measured at several environmental stress conditions (such as multiple temperatures, humidity levels, radiation levels, etc.) in order to be plotted on Arrhenius plots or other modeling techniques. Degradation criteria selected for the product may include mechanical conditions such as absolute or relative loss of elongation, chemical criteria such as absolute or relative loss of anti-oxidants or formation of by-products in the product; or they may be measurements of selected discoloration of polymers exposed to severe environmental conditions or onset of objectionable smell, taste, potency, etc. of food or pharmaceutical products. Degradation times for resistivity curves may be based on a arbitrary absolute resistivity value for each stress condition (such as each temperature), or relative resistivity values may be selected (such as relative resistivity drops) for each environmental stress conditions.

Ideally, both the resistivity vs. time at several temperatures and degradation parameter of the product vs. time are generally linear when plotted on Arrhenius plots, similar to the EPR insulation elongation—at break and EPR sensor resistivity curves of FIG. 2. In this case, a correlation exists between sensor resistivity and product degradation at a variety of degradation temperatures and the process allows prediction of remaining life of the product by measurement of resistivity at a different temperature from that measured. If activation energies are similar between the sensor and product, but time constants are different, correlations can be made mathematically or by a control agent which changes the time constant such as an anti-oxidant in the case of the EPR samples of FIG. 2.

In other cases where an Arrhenius relationship does not exist, such as non-linear Arrhenius plots, approximate correlations may be made over short temperature bands with emphasis of correlations made at environmental stress levels considered most probable. Other mathematical and statistical methods may be used to provide correlation of measured sensor resistivity and product degradation. By correlating the resistivity of the sensor with degradation of the product obtained through natural, artificial or accelerated aging of the sensor and product, condition of the product can be determined by measuring the resistivity of the sensor. For example, the degradation of a polymeric product or products utilizing polymeric portions such as cable insulation, rubber hoses, seals and gaskets, composite structure, aircraft and marine hull matrixes, plastic building materials, and certain food and pharmaceutical products may be determined by utilizing the polymeric component/s of the product as the matrix of the conductive composite degradation sensor.

Conductive particles such as carbon black, conductive carbon nanotubes, metallic particles, metallic oxide, or semiconductor particles are added to adjust the initial resistivity to the desired level. In the preferred embodiments, the conductive filler is selected to be chemically inert with the matrix and other components(s) of the sensor. In the preferred embodiments, the initial resistivity is selected in the ranges disclosed in PCT application PCT/US05/05604. In a more preferred embodiment, the initial resistivity of the sensor is selected to be approximately one-half of the difference between the upper and lower percolation thresholds on a log resistivity vs. volume fraction curve. The initial resistivity will normally be selected to be low enough to be read by field resistivity-measuring equipment but high enough to be in a steep portion of the percolation curve to provide good sensitivity of degradation measurements at ambient conditions. Initial resistivities of 1E+2 to 1E+10, more preferably, 1E+3 to 1E+8, and still more preferably between 1E+4 to 1E+7 ohm-cm initial resistivities have been found to be practical initial levels providing reasonable sensitivity and simple measurement equipment.

In sensors utilizing the same or similar polymeric component in the product as the matrix of the sensor, the polymeric component of the product itself serves as the control agent and no additional modifying control agent is normally required. In other embodiments, a modifying control agent such as an anti-oxidant may be added to provide improved degradation correlation of the sensor and product. Other reaction rate modifying control agents may be selected depending on the degradation mechanisms of the sensor conductive composite and include permeability or reactant diffusion modifiers and physical diffusion modifiers including the physical dimensions of the sensor, diffusion barriers around the sensor composite and sensor packaging.

The second approach may be used for any degradable product including non-polymeric products such as metallic and ceramic products, or products which contain both polymeric and non-polymeric components such as composite materials, propellants and certain food and pharmaceutical products. In this approach, the sensor conductive composite is "designed" to provide resistivity reduction that can be correlated to environmental stress degradation of the product being monitored. A polymeric component and, optionally, a modifying control agent are selected for the matrix of the sensor which, when compounded with a conductive particle filler, will provide a resistivity response to the environmental stress conditions which is correlatable to the degradation response of the product monitored. In the preferred embodiments, the activation energy of the sensor resistivity curve will be similar to that of the product being monitored for the environmental stress conditions used. In the more preferred embodiments, both the activation energy and the time constant of the sensor resistivity curve will be similar to that of the product being monitored for the environmental stress conditions.

One method for this approach involves selection of a polymer used in the sensor conductive composite which provides a similar response (such as activation energy) of resistivity response for the desired environmental stress conditions as the selected product. The activation energy and/or time constant may be "tuned" by addition of one or more control agents such as additional "blending" polymers, cross-linking agents, catalysts, hardeners, fillers, etc. Thermoplastic or pre-cured thermoset polymers may be used for relatively slow-degrading products such as wire and cable insulation, rubber hoses and gaskets, polymeric building materials, etc. Curing reactions of thermosets such as epoxies or polyesters may be used for modeling relatively fast-degrading products such as food or pharmaceuticals.

Another method of this approach would utilize a volatile component in the conductive composite sensor to adjust the sensor response to the degradable product. For example, volatile hydrocarbons, compounded with a polymeric resin and conductive fillers could provide a short or long-term degradation sensor. Volatile components such as hydrocarbons may be selected as control agents to determine the activation energy or reaction rate of the sensor response. The volatile agents can be single components, or blended to provide the desired response. Additional agents such as sensor conductive composite fillers or polymeric components which control the permeability or diffusion constants of the composite, and therefore the temperature-dependent loss of volatile fractions provide another means to "tune" the response of the sensor. Permeability barriers, compounded with the sensor element or surrounding the sensor element or sensor or product packaging may also act as a mechanical control agent to control the response of the sensor.

Figure 6:
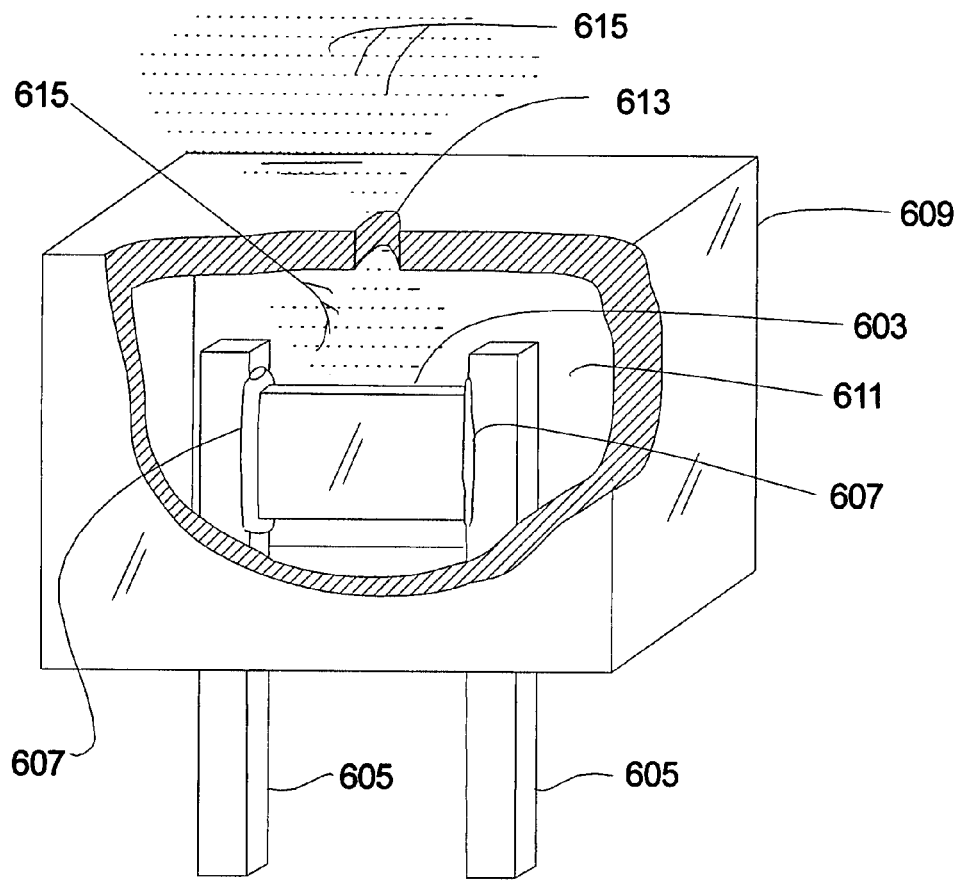
FIG. 6 is a perspective drawing of a discrete degradation sensor 601 having sensor element 603 connected to a pair of electrodes 605 for connection to a resistance measuring device.

Degradation sensors may be discrete components, or they may be integrated into the product they are monitoring. FIG. 6 is a perspective drawing of a discrete degradation sensor 601 having sensor element 603 connected to a pair of electrodes 605 for connection to a resistance measuring device (not shown). Sensor element 603 is a conductive composite comprising a polymeric matrix, conductive particles and a control agent as described earlier. Sensor element 603 may be compounded and extruded, cast or otherwise formed.

Figure 6A:
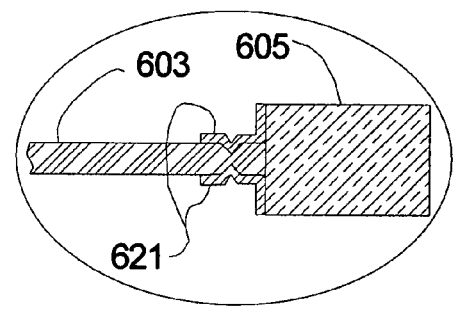
FIG. 6A is a detail perspective drawing showing a mechanical clamp method of electrically and mechanically attaching the sensor element to the electrode.

A conductive adhesive, such as a conductive epoxy 607 may be used to mechanically and electrically connect electrodes 605 to sensor element 603. In other embodiments, other means may be used to connect sensor element 603 to electrodes 605 such as mechanical clips, 621 of FIG. 6A.

In the preferred embodiments, a housing or case 609 surrounds sensor element 603 to provide mechanical protection for sensor element 603. In the preferred embodiments, case 609 comprises a cavity 611 surrounding element 603. Opening 613 allows communication of the outside environment, represented by particles 615 with cavity 611 and sensor element 603 so that sensor 603 comprises a similar environment as the product it is monitoring.

FIG. 7A is a perspective drawing showing electrical contact measurement of composite degradation sensors 701A distributed on a degradable product 703A. Sensors 701A are conductive composites made of a polymeric component, a conductive filler, and a control agent as discussed previously. In a preferred embodiment of the invention, sensors 701A are conductive adhesives utilizing a polymeric component of product 703A in sensor 701A. The adhesive component may be a hot-melt adhesive component or it may comprise a thermoset or thermoplastic component providing adhesive properties to sensors 701A for attaching the sensors to degradable product 703A. FIG. 7D is a detail cross section showing an alternative embodiment utilizing an adhesive element such as an adhesive strip 705 to provide adhesion of sensor 701A to product 703A.

A resistance measuring instrument 707 having a pair of electrodes 709 provides a means to measure the resistance of sensors 701A. Electrode 709 spacing and geometrical sizing of sensors 701A allows conversion of resistance reading of instrument 707 to resistivity for comparison of aging models. Simple contact of electrodes 709 of instrument 707 on sensors 701A provides a quick means to make resistance measurements as shown by arrows 711. Degradable product 703A may be any degradable product for which degradation properties have been correlated to sensor 701A resistivity response in a controlled degradation environment. In alternative embodiments, resistance-measuring instrument 707 incorporates the features of wired resistance measuring instruments 1103 and 1123 of FIGS. 11A and 11B.

FIG. 7B is a perspective drawing showing electrical contact measurement of composite degradation sensors 701B distributed on a degradable product 703B. Sensors 701B are conductive composites made of a polymeric component, a conductive filler, and a control agent as discussed previously. In a preferred embodiment of the invention, sensors 701B are conductive composites utilizing a polymeric component of degradable product 703B. Sensors 701B may be cast or co-extruded into product 703B and have at least one surface 702B on an outside surface 703B1 or otherwise accessible portion of, degradable product 703B to allow sensor resistance measurements.

FIG. 7C is a perspective drawing showing electrical contact measurement of composite degradation sensor 701C distributed on a degradable product 703C. Sensor 701C is conductive composites made of a polymeric component, a conductive filler, and a control agent as discussed previously. In a preferred embodiment of the invention, sensor 701C is a conductive composite utilizing a polymeric component of degradable product 703C. Sensor 701C may be cast, molded or co-extruded into product 703C and has at least one surface 702C on an outside surface 703C1 or otherwise accessible portion of degradable product 703C to allow sensor resistance measurements.

Figure 8A:
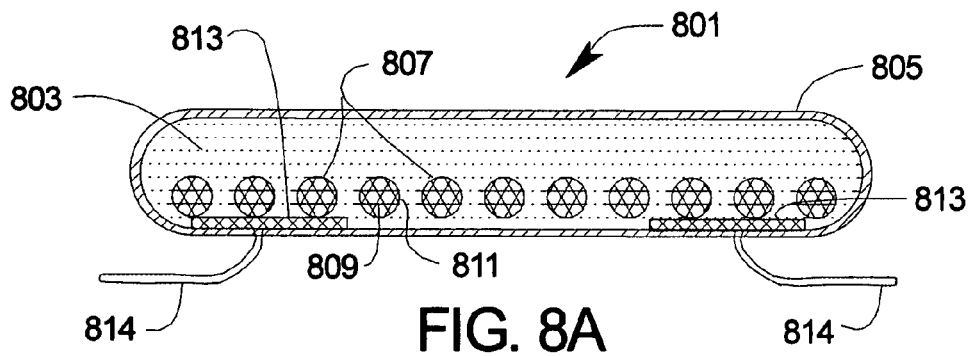
FIG. 8A is a cross section of a degradation sensor comprising multiple components of a sensor conductive composite disposed in a flexible bag or pouch.

FIG. 8A is a cross section of degradation sensor 801 comprising sensor element or sensor conductive composite 803 disposed in a flexible bag or pouch 805. Conductive composite 803 comprises a polymeric component and a conductive filler as described earlier. In the preferred embodiments, conductive composite 803 is a liquid or gel. Control elements 807 comprise a control agent 809 such as a catalyst or hardener encased in a breakable shell 811. Control agent 809 is chosen to provide the degradation reaction desired to model a degradable product (not shown). Electrodes 813 mounted internally of pouch 805 connect to wires 814 to provide a means to measure resistance through conductive composite 803.

Figure 8B:
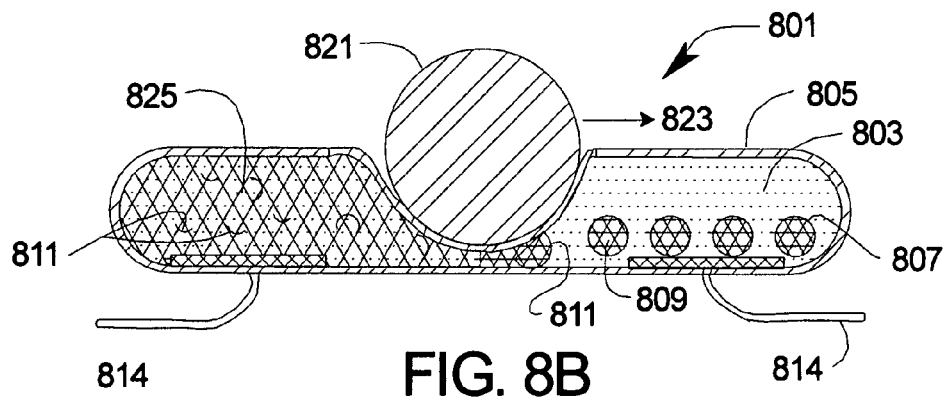
FIG. 8B shows a means to activate the degradation sensor of FIG. 8A by mechanical mixing.

FIG. 8B shows a means to activate degradation sensor 801 by mechanical mixing. Roller 821, rolled and pressed over pouch 805 as shown by arrow 823 breaks shells 811 of control elements 807, releasing control agent 809 and mixing with sensor conductive composite 803 to produce activated conductive composite 825.

Figure 9A:
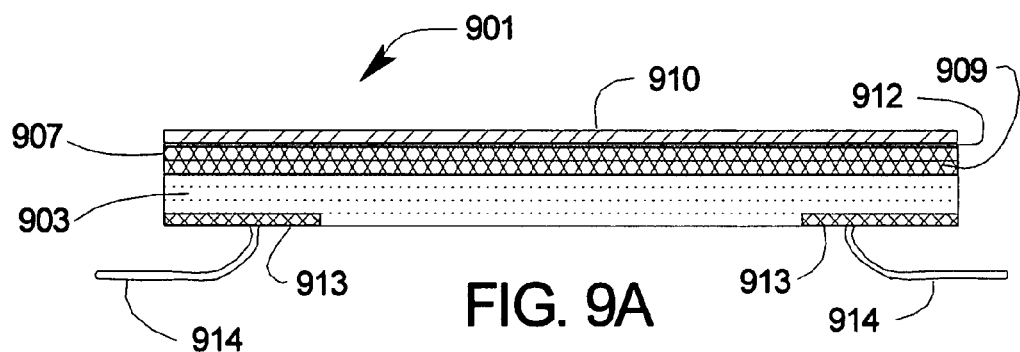
FIG. 9A is a cross section of a degradation sensor comprising an activation strip containing a component of the sensor composite.

FIG. 9A is a cross section of degradation sensor 901 comprising sensor element or sensor conductive composite 903. Sensor composite 903 comprises a polymeric component and a conductive filler as described earlier. In the preferred embodiments, conductive composite 903 is a porous solid. Control strip or element 907 comprises a control agent 909 such as a catalyst or hardener in the form of a gel or liquid. Control agent 909 is chosen to provide the desired degradation reaction to model a degradable product (not shown). Protective strip 910, attached by adhesive 912, provides mechanical protection of control element 907 from damage due to normal handling. Electrodes 913 and wires 914 provide a means to measure resistance through conductive composite 903.

Figure 9B:
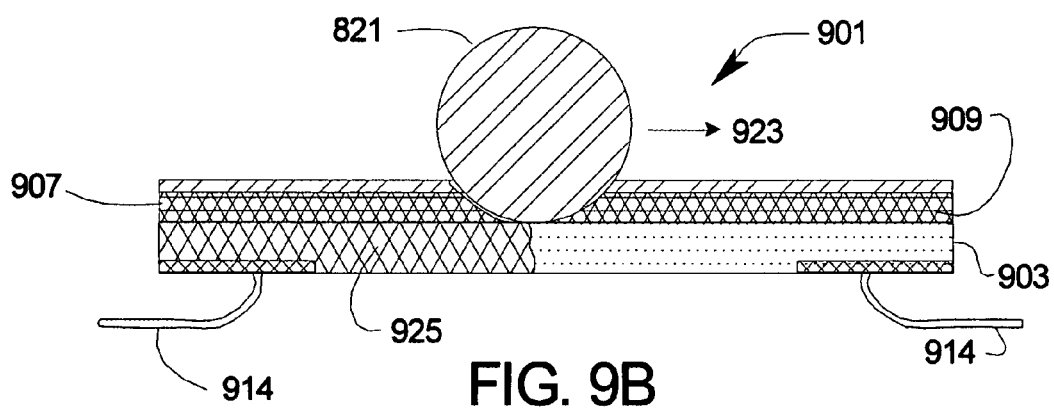
FIG. 9B shows a means to activate the degradation sensor of FIG. 9A by mechanical mixing.

FIG. 9B shows a means to activate degradation sensor 901 by mechanical mixing. Roller 821, rolled and pressed over control element 907 as shown by arrow 923, presses control agent 909 into conductive composite 903 and mixes with sensor conductive composite 903 to produce activated conductive composite 925.

Figure 10A:
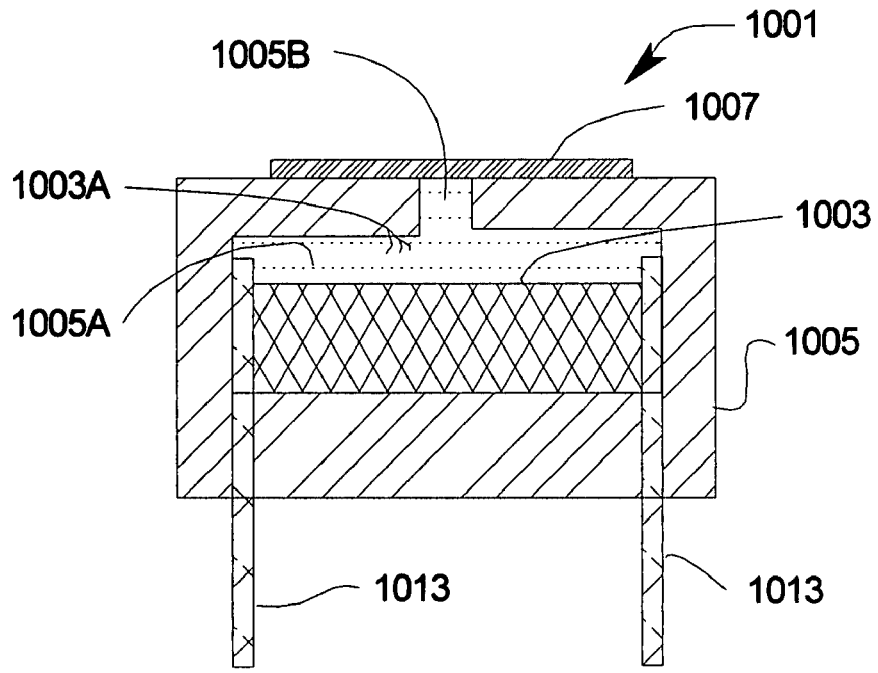
FIG. 10A is a cross section drawing of a degradation sensor having a sensor conductive composite enclosed in a holder or case.
Figure 10B:
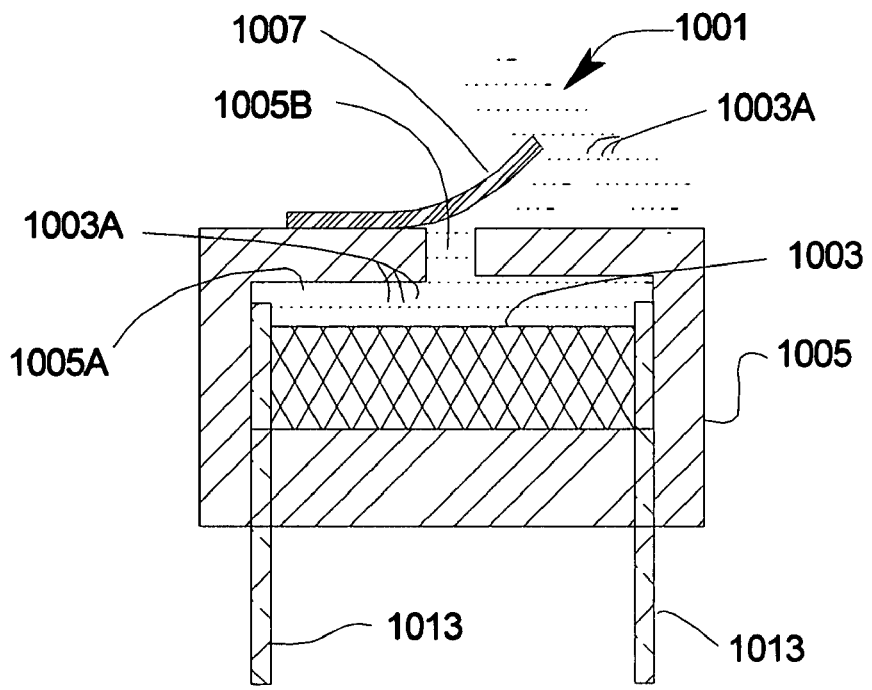
FIG. 10B is the sensor of FIG. 10 activated by removal of a peel strip.

FIG. 10A is a cross section drawing of degradation sensor 1001 having sensor conductive composite 1003 enclosed in a holder or case 1005. In the preferred embodiments, sensor conductive composite 1003 includes a volatile agent such as a volatile hydrocarbon whose mass loss (demonstrated by evaporated particles 1003A in case void 1005A of FIG. 10A) is caused by the environmental conditions of the sensor such as temperature and humidity. Conductive composite 1003 may be a solid, liquid or gel. During inactive periods, loss of the volatile agent particles is prevented by impermeable peel strip 1007 covering aperture 1005B of case 1005. Upon activation of sensor 1001, peel strip 1007 is removed as shown in FIG. 10B, allowing volatile agent or evaporated particles 1003A to escape through aperture 1005B, resulting in a resistance response as measured by electrodes 1013.

Figure 10C:
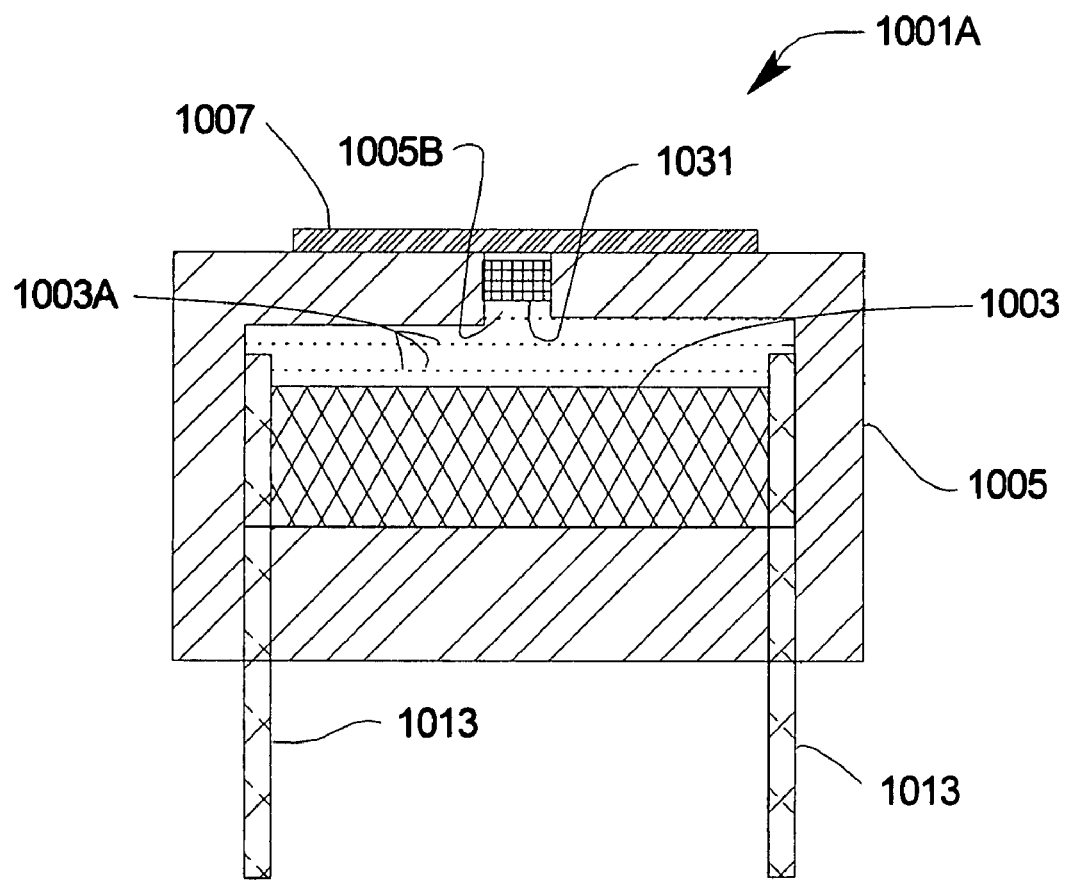
FIG. 10C is a cross section drawing of a degradation sensor having a diffusion control element disposed in an aperture of the sensor case.

FIG. 10C is a cross section drawing of degradation sensor 1001A having a diffusion control element 1031 disposed in aperture 1005B. Diffusion control element 1031 may be permeable or semi-permeable to the volatile agent used in the sensor, evaporated particles of which 1003A are shown in the figure. The amount of permeability of control element 1031 to volatile or evaporated particles 1003A can be selected to provide the desired degradation response such as resistance vs. time at selected temperatures. The sensor may be made inactive by use of peel strip 1007 that is essentially impermeable to volatile agent or evaporated particles 1003A.

Modeling of degradation by use of a volatile agent may be carried out in a number of ways. For example, if modeling a degradable product whose primary degradation stress is temperature, the volatile agent may be selected which provides a similar activation energy of resistance response of the sensor element as the selected degradation measurement of the product. Additionally, the time constant of the sensor response can be adjusted by selecting the diffusion response of diffusion control element 1031.

Sensor activation of slow acting degradation reactions is not critical since the degradation of the sensor and product before either sensor-product association or acquisition and use by the end user is small compared to the lifetime of the product. For example, the degradation (and resulting sensor resistance decrease) of a sensor made of a conductive composite of a wire and cable insulation polymer before its assembly in a wire or cable product is small compared to the degradation (and resulting sensor resistance decrease) over the total lifetime of the wire or cable. Manufacturing the sensor to a standardized initial resistance or measuring the initial resistance after sensor manufacture may be sufficient in degradation models to determine actual wire and cable degradation at any point during the lifetime.

For products having a relatively short lifetime such as fresh foods, agricultural products, pharmaceutical products and single part adhesives; sensor (and product) degradation (and resulting sensor resistance decrease) before sensor attachment or association to the product may be considerable. For these applications, the degraded sensor resistance may be measured at the time of sensor-product association such as when the actual product is manufactured or when the sensor is applied to a newly produced product. In this way, sensor degradation before sensor-product association can be compensated by the sensor-product degradation models to account for actual product degradation.

A second method of associating a sensor and a product for a fast-degrading product is to provide a means to delay degradation of the sensor, and then "activate" the sensor at the time of product manufacture or packaging. For example, the sensor for a food product may be stored at a significantly reduced temperature (therefore reducing the sensors rate of degradation) until it is attached during the packaging of the food product. Or, a sensor utilizing a two-part curing resin may maintain separation of the resin parts (as shown in FIG. 8A or 9A) until attached to, or otherwise associated with, the product. Sensor activation upon product association would include mixing of the two parts as shown in FIGS. 8B and 9B. Or, in the case of a volatile mass-loss sensor, the sensor diffusion may be minimized by cooling or by covering of ventilation apertures until sensor-product association as shown in FIGS. 10A and 10C.

Figure 11A:
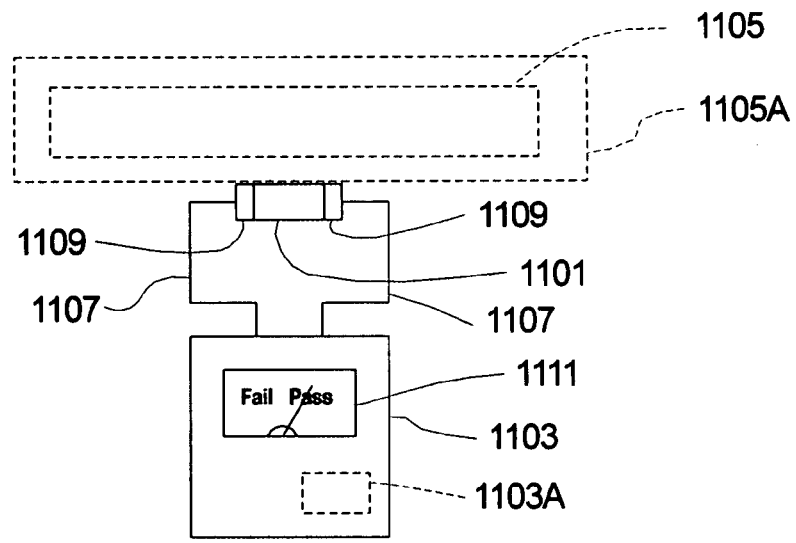
FIG. 11A is a block diagram of a method of sensor communication where an electrical property-measuring device such as resistance measuring instrument is used to measure the resistance of degradation sensor.

FIG. 11A is a block diagram of a method of sensor communication where an electrical property-measuring device such as resistance measuring instrument 1103 is used to measure the resistance of degradation sensor 1101. Degradation sensor 1101 is a conductive composite sensor as described in the previous sections. Degradation sensor 1101 is associated with degradable product 1105 by attaching or incorporating sensor 1101 into the product, or attaching sensor 1101 to product packaging 1105A. Electrical connections such as conductors 1107 are used to connect electrodes 1109 of sensor 1101 to resistance measuring instrument 1103.

In the preferred embodiments, resistance-measuring instrument 1103 is calibrated to correlate resistance of sensor 1101 and indicate the degradation state or remaining life of product 1105. Correlation may be done by calibrating the indicator, such as a meter face 1111 in an analog indicator with a degradation state or pass/fail threshold; or it may indicate remaining life depending on an assumed environmental condition. Or, in the case of a digital resistance measurement, the desired degradation state and/or remaining life output may be correlated by a microprocessor 1103A internal to resistance measuring instrument 1103. Microprocessor 1103A may be programmed to correlate resistance measurements with degradation models stored in the memory of microprocessor 1103A. Alternatively, a resistance measurement by instrument 1103 may be correlated to product degradation by use of an external correlation means such as a correlation chart, indicator or computer.

Figure 11B:
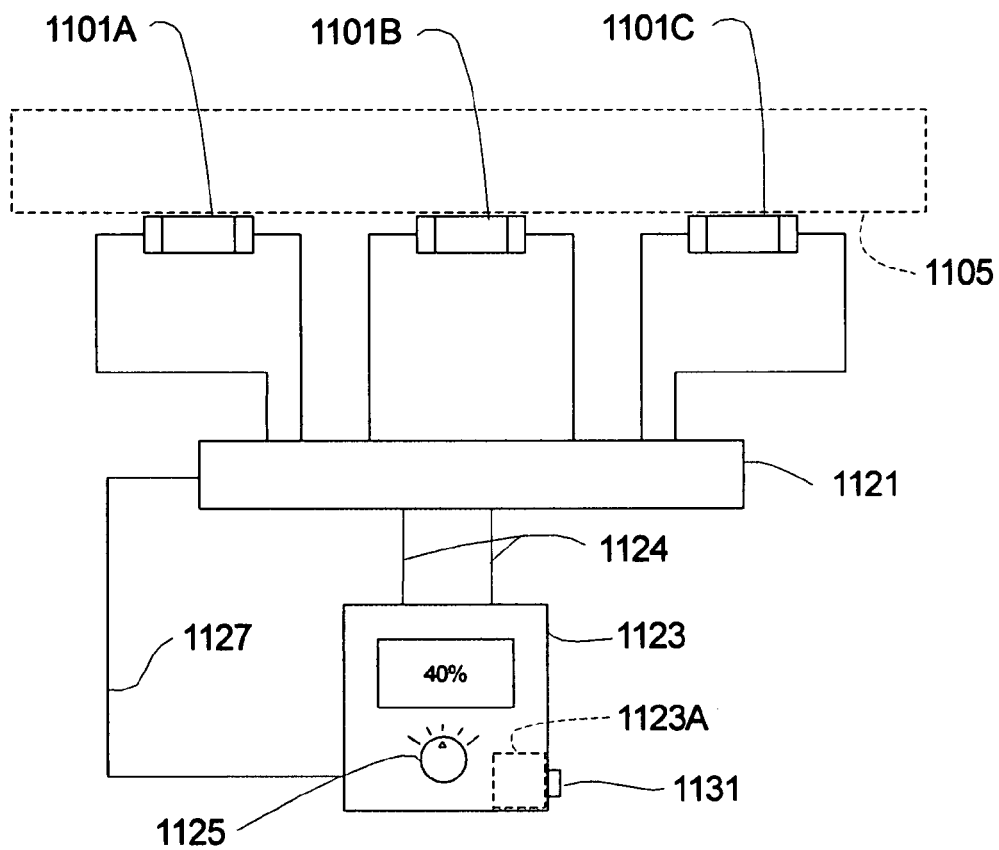
FIG. 11B is a block diagram of an alternative embodiment of a sensor communications method utilizing a multiplexer to connect multiple degradation sensors associated with a product to resistance measuring instrument.

FIG. 11B is a block diagram of an alternative embodiment of a sensor communications method utilizing a multiplexer 1121 to connect multiple degradation sensors 1101A, 1101B, 1101C, associated with product 1105, to resistance measuring instrument 1123. Multiplexer 1121 receives inputs (wired or wireless) from each sensor and provides a selected output to instrument 1123 through connections 1124. A selector switch 1125 and multiplexer communications connection 1127 allows interrogation of the desired sensor. Alternatively, a manual selector switch may be substituted for multiplexer 1121. Microprocessor 1123A may be programmed to correlate resistance measurements with degradation models stored in the memory of microprocessor 1123A. A communications connection 1131 provides a means to communicate sensor resistance and product degradation status to a computer or network.

Figure 11C:
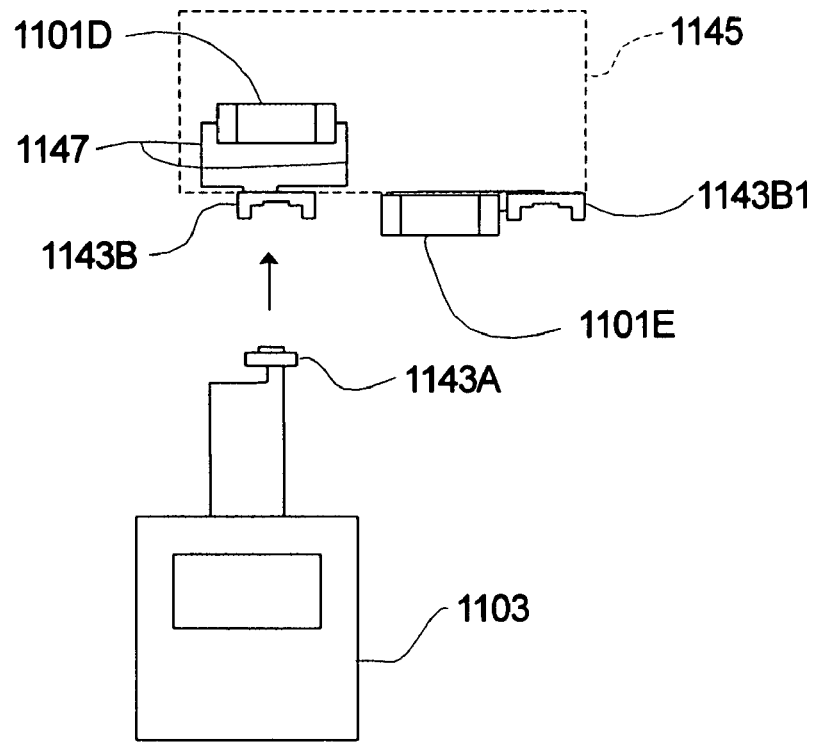
FIG. 11C is a block diagram of a method of sensor communication using electrical connectors such as quick connectors to communicate degradation data from sensors.
Figure 11D:
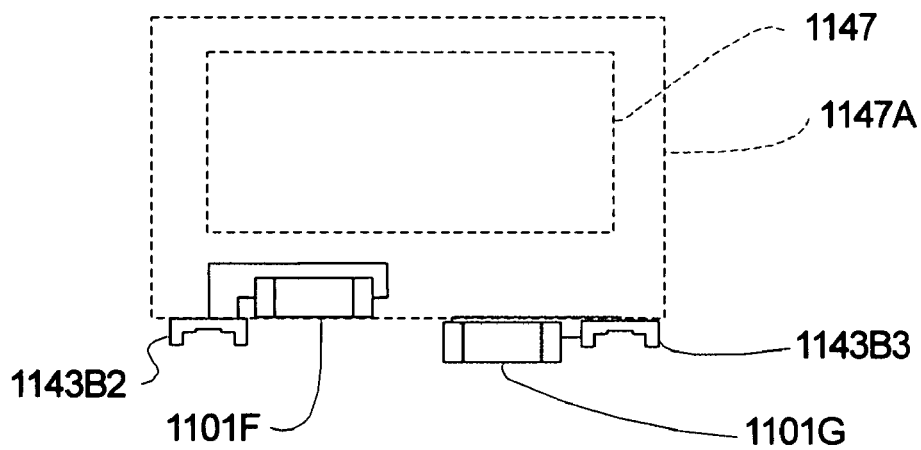
FIG. 11D is an embodiment of sensor communication showing sensors located between a product being monitored and the product package, and a sensor located outside the product package, both using quick-connect connectors for sensor communication.

FIG. 11C is a block diagram of a method using electrical connectors such as quick connectors to communicate degradation data from sensors. A connector portion, such as male connector 1143A connected to resistance measuring instrument 1103 provides a means of temporary connection to complementary connector portions or female connectors 1143B. Sensor 1101D may be internal to product 1145 and connected to respective connector 1143B, external to product 1145, by conductors 1147. Or, sensor 1101E may be mounted external to product 1145 and connected by conductors to connector 1143B1. Sensor 1101F, mounted external to product 1147 but internal to product packaging 1147A and sensor 1101G, mounted external to product packaging 1147A are connected to respective connectors 1143B2 and 1143B3 by conductors as shown in FIG. 11D.

Figure 12A:
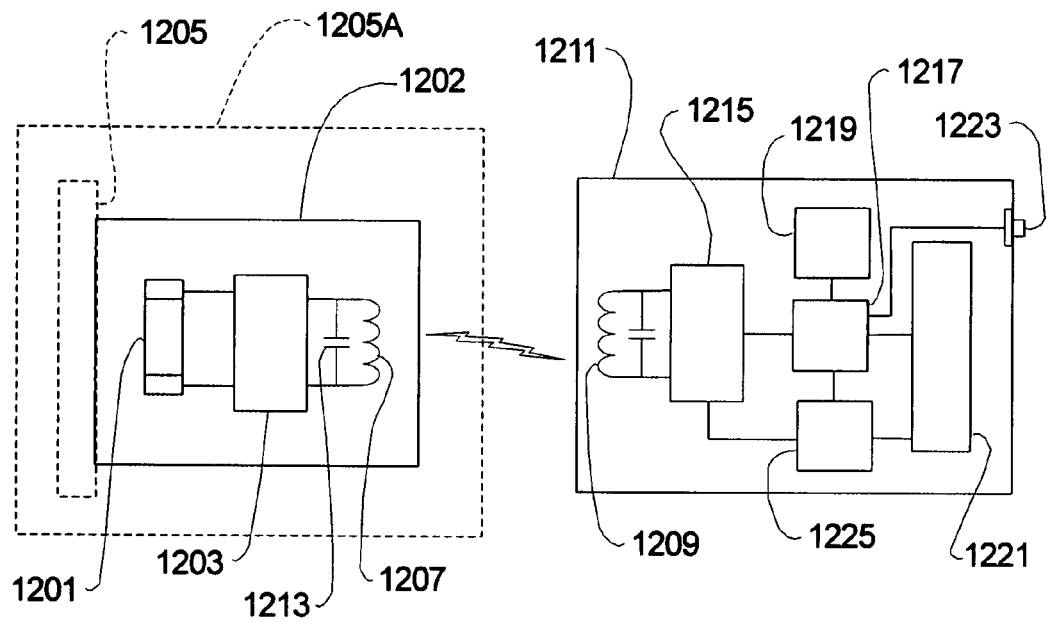
FIG. 12A is a block diagram of a wireless communications method used to determine degradation of a product inside product packaging.

FIG. 12A is a block diagram of a wireless communications method used to determine degradation of a degradable product 1205 inside product packaging 1205A. Sensor 1201, comprising a conductive composite as discussed in earlier embodiments, is attached to a wireless communications device such as a passive RFID chip 1203. In the preferred embodiments, RFID 1203 comprises a non-volatile memory and a sensor input such as RFID chip MCRF 202 by Microchip Inc. Inductor or antenna 1207 communicates with inductor or antenna 1209 of RFID reader 1211 and provides power to the RFID circuits of RFID assembly 1202. Tuning capacitor 1213 provides RF tuning of RFID assembly 1202 with the tuning circuits of reader 1211. Product 1205 identification information is programmed into the non-volatile memory of RFID 1203.

Reader 1211 comprises a modulator/demodulator 1215 connected to antenna 1209. A microprocessor 1217 provides control, memory and calculation operations for reader 1211. Input device 1219 provides a means to program and initiate microprocessor 1217 routines, and display 1221 provides a means to display sensor 1201 output as well as RFID 1203 and reader 1211 status. Communications connector 1223, connected to microprocessor 1217 allows communication with a network or separate computer. A power supply, such as a battery 1225, provides power to the circuitry, and by the radio frequency communication, RFID assembly 1202. In other embodiments, RFID assembly 1202 is an active RFID with internal volatile memory. The wireless communication allows monitoring of sensor 1201 for product 1205 inside packaging 1205A without conductor penetration of packaging 1205A.

Figure 12B:
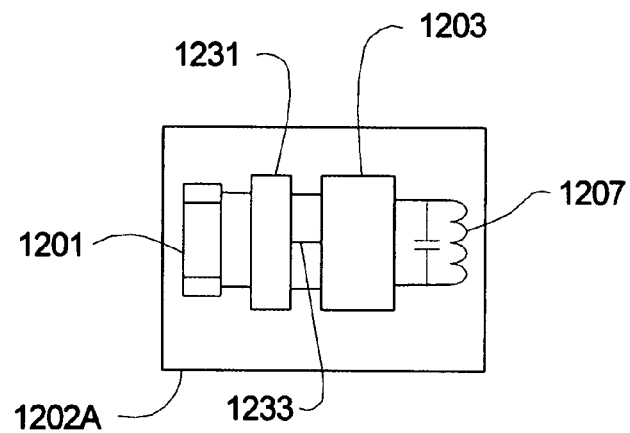
FIG. 12B is a block diagram of an alternative embodiment of an RFID assembly for a degradation sensor having a resistance threshold detector between the sensor and the RFID chip.

FIG. 12B is a block diagram of an alternative embodiment of RFID assembly 1202A for sensor 1201 having a resistance threshold detector 1231 between sensor 1201 and RFID chip 1203. Threshold detector 1231 is powered by RF energy via RFID chip 1203 and conductor 1233 and provides a binary input to RFID chip 1203 depending on the resistance of sensor 1201 and one or more reference resistors in threshold detector 1231.

Figure 12C:
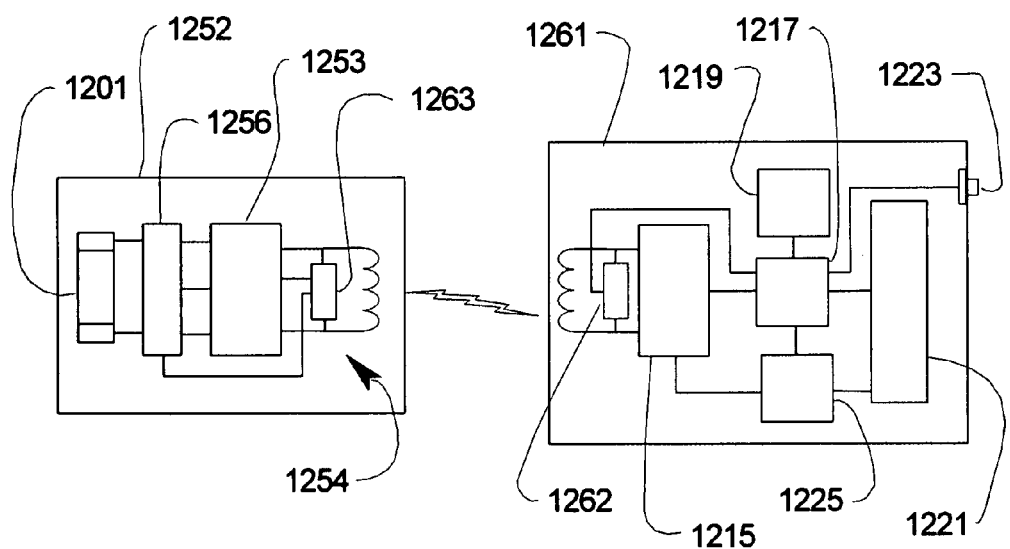
FIG. 12C is a block diagram of a passive RFID assembly and reader utilizing variable frequency tuning to determine sensor resistance.

FIG. 12C is a block diagram of a passive RFID assembly 1252 and reader 1261 utilizing variable frequency tuning to determine sensor 1201 resistance. Voltage divider 1256 of RFID assembly 1252, receiving a reference voltage from passive RFID chip 1253 provides a voltage input to voltage variable capacitor 1263 depending on sensor 1201 resistance.

In a similar manner, voltage variable capacitor 1262 of reader 1261 forms a variable frequency tuning circuit for reader 1261. Microprocessor 1217 of reader 1261 provides a sweep voltage (via a digital to analog converter, not shown) to voltage variable capacitor 1262 and compares the resulting amplitude or phase of the induced response from RFID tuned antenna circuit 1254 to determine the resonant frequency (and therefore sensor resistance) of RFID assembly 1252. Microprocessor 1217 compares the resulting sensor resistance with a correlation model to provide product degradation information via indicator or display 1221. Other passive or active wireless means may be used to communicate sensor 1201 resistance for correlating degradation data such as utilizing active RFIDs, radio frequency, visible frequency, infrared or ultrasonic frequency transmitters and receivers.

Figure 13:
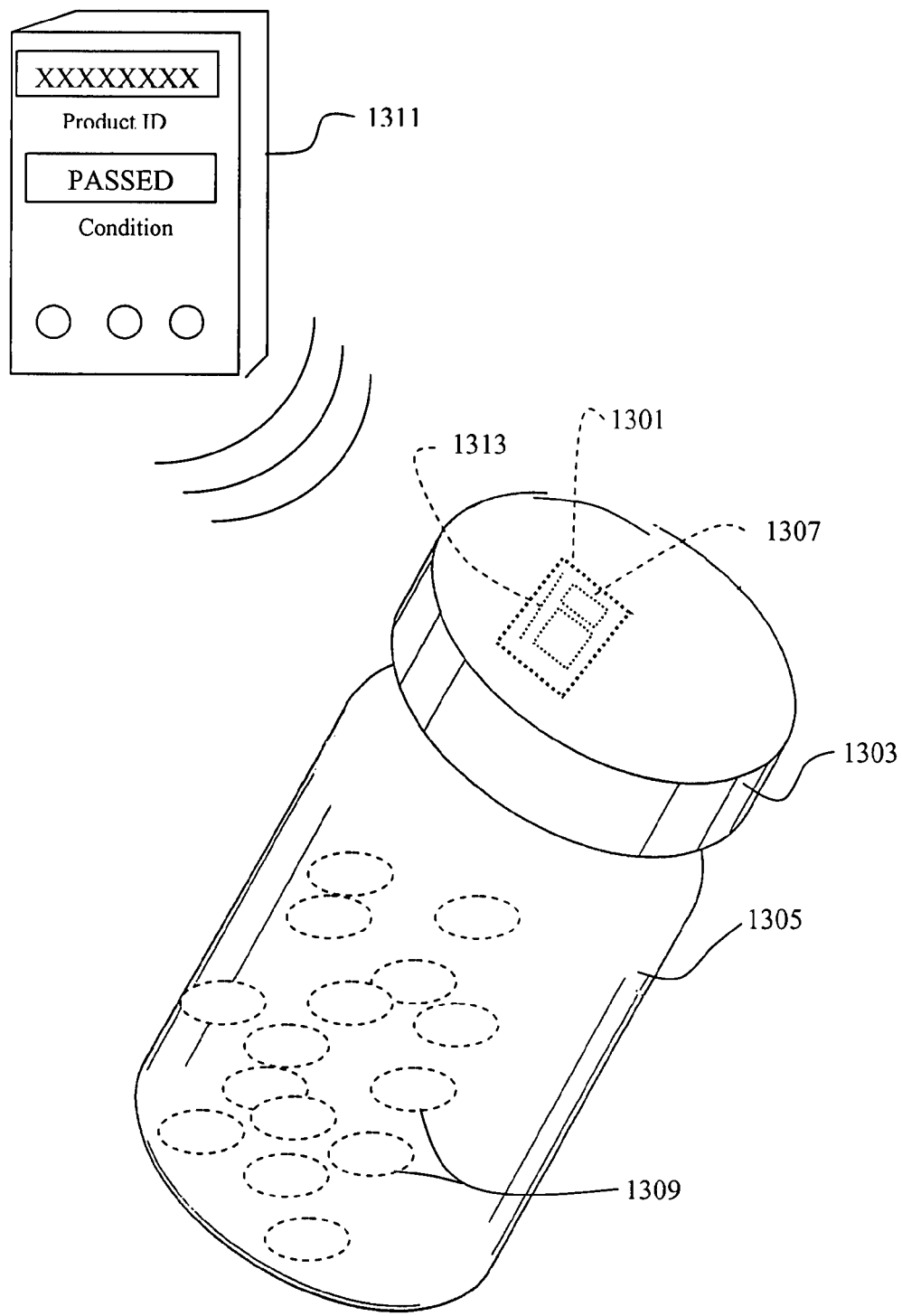
FIG. 13 is a perspective drawing of RFID assembly attached to an inside surface of the cap of a product container.

Wireless communication with degradation sensors allows an improved method of monitoring product degradation within protective packaging or containers. FIG. 13 is a perspective drawing of RFID assembly 1301 attached to an inside surface of cap 1303 of container 1305. Sensor 1307 of RFID assembly 1301 is a conductive composite sensor as discussed previously, and whose resistance-time characteristics are correlatable to degradation of product such as food or pharmaceutical product 1309. By placement of sensor 1307 inside container 1305, sensor 1307 is exposed to the same environment as product 1309, regardless of condition or damage to container 1305. Reader 1311 communicates wirelessly via antenna 1313 of RFID 1301 through container 1305 and provides product ID and product condition by modeling techniques discussed previously. In still other embodiments, contact or connector methods, discussed previously, may be employed with sensors mounted inside or outside container 1305.

Figure 13A:
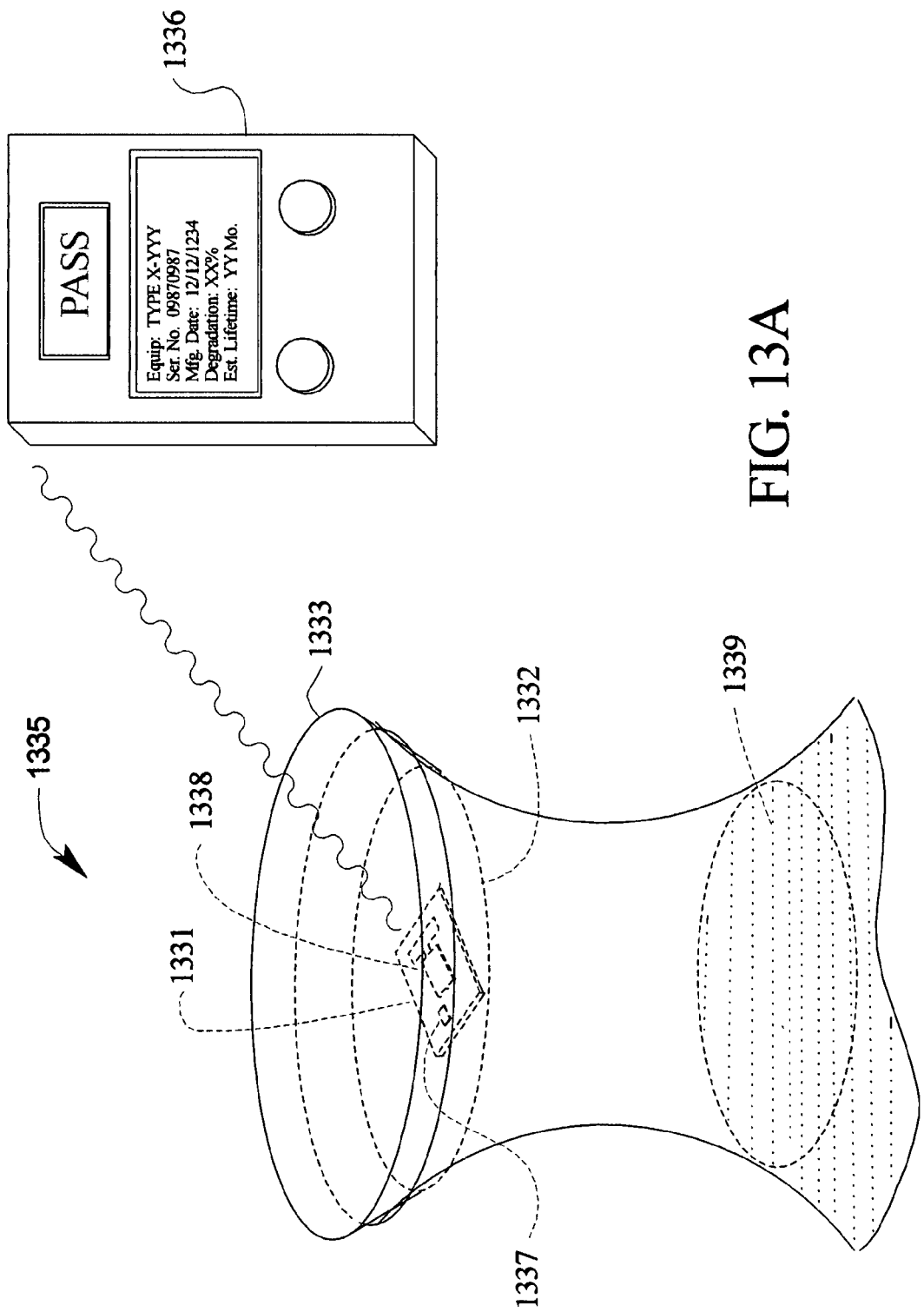
FIG. 13A is a perspective drawing of RFID assembly attached to an inside surface of a nozzle cap of solid propellant motor.

FIG. 13A is a perspective drawing of RFID assembly 1331 attached to an inside surface 1332 of nozzle cap 1333 of solid propellant motor 1335. Sensor 1337 of RFID assembly 1331 is a conductive composite sensor as discussed previously, whose resistance-time characteristics are correlatable to degradation of a limiting degradable component of propellant 1339 such as the binder of the propellant. By placement of sensor 1337 inside the nozzle cap 1333 of motor 1335, sensor 1337 is exposed to the same environment as propellant 1339, regardless of condition or damage to nozzle cap 1333.

Reader 1336 communicates wirelessly with RFID assembly 1331 through motor 1335 and/or cap 1333 and provides product ID and product condition by modeling techniques discussed previously. For example, reader 1336 can provide equipment identification, serial number, manufacturing date and other product identification information from data programmed into the non-volatile memory of RFID chip 1338.

By processing sensor 1337 resistance data and comparing to algorithms of a microprocessor of reader 1336, the reader can also provide a Pass/Fail condition of the propellant, a degradation percentage for the propellant, and by inputting or measuring current ambient temperature into reader 1336, it can also provide an estimated remaining lifetime of the propellant.

Figure 13B:
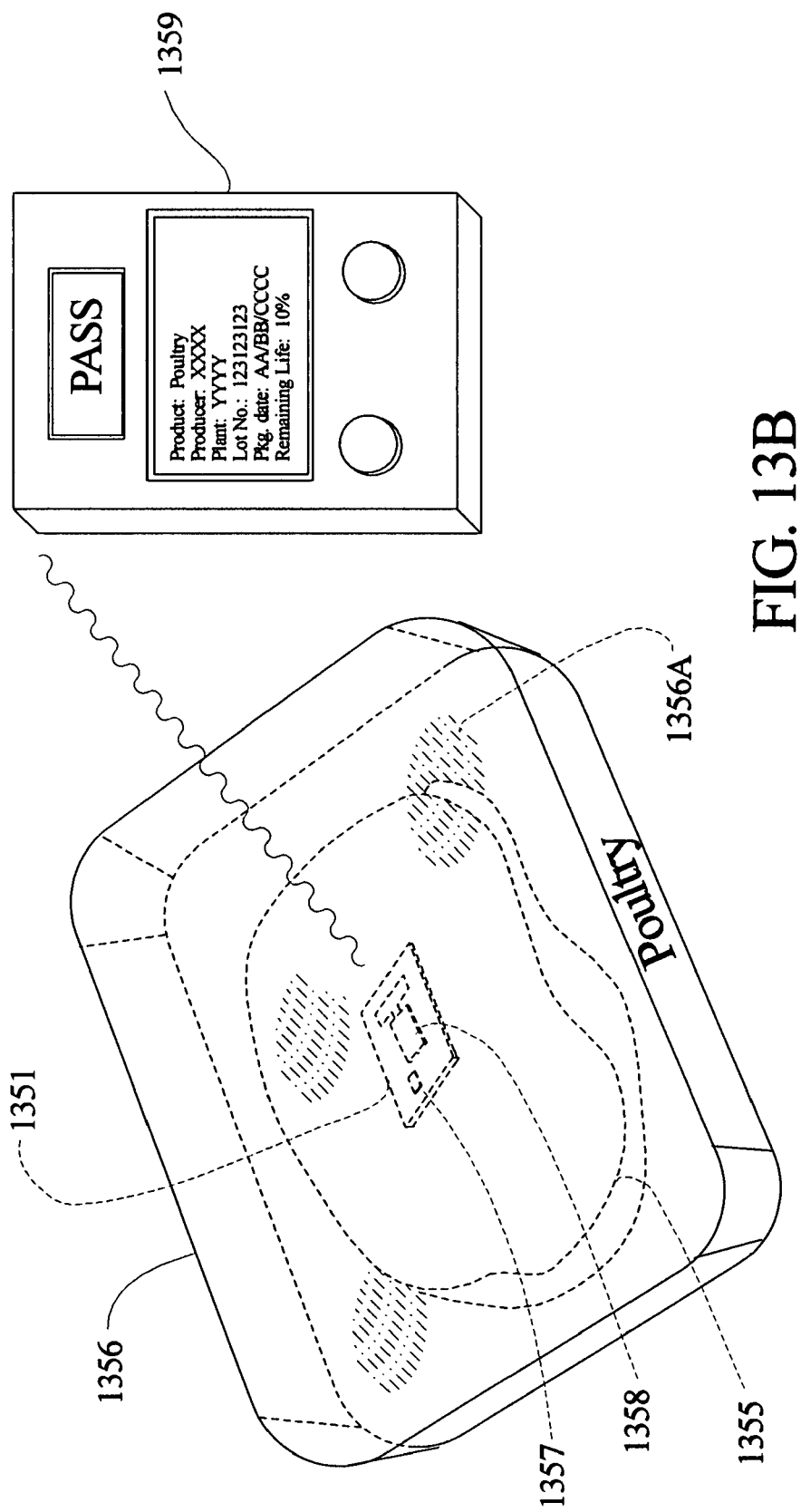
FIG. 13B is a perspective drawing of a method of monitoring the identification and condition of a food product such as fresh poultry by wireless communication with a degradation sensor attached to a RFID.

FIG. 13B is a perspective drawing of a method of monitoring the condition of a food product such as fresh poultry 1355 packaged in package 1356. RFID assembly 1351, containing degradation sensor 1357 and passive RFID chip 1358 is attached to an inside surface of transparent film 1356A of package 1356 and communicates with reader 1359. Sensor 1357 is a conductive composite sensor as discussed previously, whose resistance-time characteristics are correlatable to degradation of poultry in varying environments such as temperature and oxygen level. By placement of sensor 1357 inside package 1356, sensor 1357 is exposed to the same environment as poultry product 1355, regardless of condition or damage to package 1356.

Reader 1359 communicates with RFIC assembly 1351 as previously discussed and provides product identification data such as type of food product, producer, packaging plant identification, lot number, and packaging date. By processing sensor 1357 resistance data and comparing to algorithms of a microprocessor of reader 1359, the reader can also provide a Pass/Fail condition of the poultry, a remaining life percentage, and by inputting or measuring current ambient temperature and, optionally, other environmental conditions into reader 1359, it can also provide an estimated remaining lifetime or expiration date of the food product.

Figure 14:
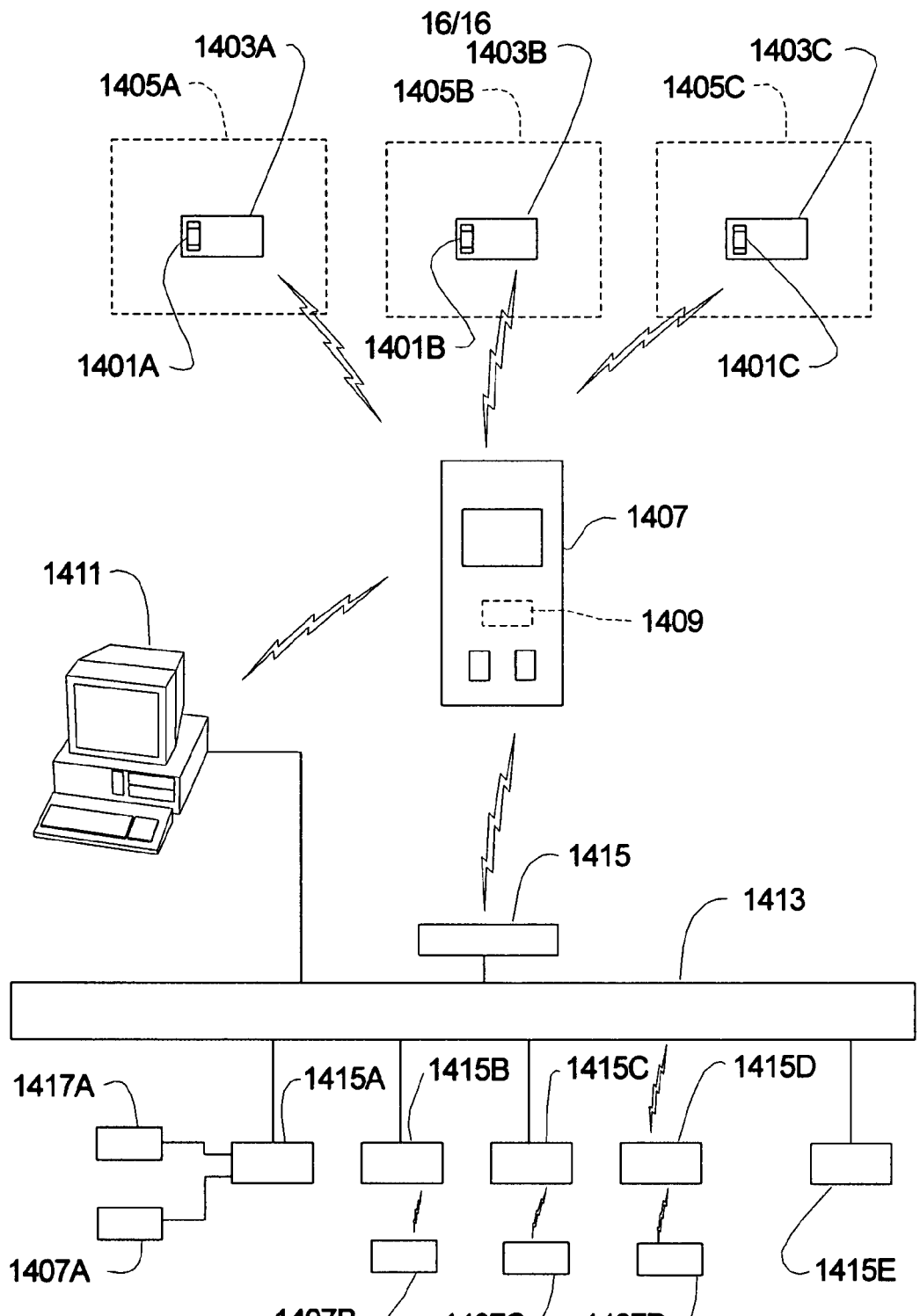
FIG. 14 is a block diagram of a method for tracking degradable products and determining their condition incorporating a network of users.

FIG. 14 is a block diagram of a method for tracking degradable products and determining their condition. Sensors 1401A, 1401B and 1401C are disposed in or on respective degradable products 1405A, 1405B, 1405C or product packaging as disclosed in previous embodiments. A sensor communications device such as RFID reader 1407 communicates with sensors 1401A, 1401B, 1401C via RFID assemblies 1403A, 1403B, 1403C.

Product data such as product identification, manufacturer, lot number, manufacturing and packaging date is programmed in the memory, such as volatile or non-volatile memory of the respective RFID assemblies at a preselected time, such as following manufacture, packaging, distribution or sale of the product. In other embodiments, sensor 1401A, 1401B, 1401C information is also programmed into the memory such as initial sensor resistance (or resistivity), along with resistivity-degradation correlation data.

In the preferred embodiments, RFID reader 1407 contains a microprocessor 1409 to correlate sensor resistance from the respective sensors in the products to the degraded condition of the respective product as discussed previously. Microprocessor 1409 correlates the resistance of the sensors to a correlation model programmed into the microprocessor. The resulting product identification and degradation condition may be used by an operator in the field, or the data may be uploaded into a computer 1411 by wired or wireless communication for storage or processing. Or, degradation condition and product identification data may be communicated directly to a network 1413 via a wired or wireless interface 1415, or by computer 1411 communicating with reader 1407. Network 1413 may be a local network or it may be an intranet or the Internet and allows two-way communication with reader 1407 from multiple users 1415A, 1415B, 1415C, 1415D and 1415E.

Use of a network such as network 1413 allows great flexibility in the use of degradable sensors. For example, network user 1415A may be a manufacturer or packager of degradable product 1405A and programs product identification data, and optionally, sensor 1401A initial resistance data in RFID assembly 1403A via programmer 1417A. Network user 1415A can also access product and sensor data by use of a reader 1407A. Network user 1415B may be a product user such as a wholesaler or distributor who can read product ID and sensor 1401A data via reader 1407B. Optionally, through access of network 1413 user 1415B can access initial resistivity or correlation model data from the manufacturer network user 1415A.

Likewise, network user 1415C may be a retailer who can read product ID and sensor 1401A data via reader 1407C. Optionally, through access of network 1413 user 1415C can access initial resistivity or correlation model data from the manufacturer network user 1415A or prior resistivity (degradation) data from user 1415B. Network user 1415D may be a customer or final end-user who through use of wireless reader 1407D can read product ID and sensor 1401A data. Optionally, prior sensor data from all users is accessible through network 1413.

Network 1413 also allows improved security and tracking of product 1405A, 1405B and 1405C product degradation throughout the chain of network users 1415A, 1415B, 1415C and 1415D. For example, a manufacturer, through uplinks of sensor data from other network users can track the amount of product degradation by each user throughout product life. Optionally user 1415E is a network administrator or a regulatory agency. Security codes and password procedures and software limits access of specified data to authorized users.

The apparatus and methods of the environmental sensor as discussed can be used for virtually any product which degrades by selecting an appropriate polymer matrix, a control agent, and a conductive filler, and then modeling the sensor resistivity with a selected product degradation measurement taken at multiple controlled environmental conditions. The control agent may be the selection of a polymer matrix which has the same or similar polymeric component or components as the product it is monitoring. Or, the control agent may incorporate chemical, physical or biological control of degradation reactions which allow correlation with the product degradation.

Products which are well adaptable to the environmental degradation sensor of the methods disclosed herewith include, but are not limited to: wire and cable products, electrical and electronic components, composite materials used in aerospace, marine, and terrestrial vehicle applications, rubber and plastic hoses and pipe, belts, tires, automotive, marine and aircraft interior components, polymeric construction and building products such as plastic siding, plastic and asphalt roofing, decking and fencing, safety equipment such as life rafts, life preservers, foul weather gear, parachutes, rope and cable systems, bio-medical components such as blood, plasma and IV bags and containers, hoses, valves, artificial limbs and organs, medical gloves, medical dressings and laboratory coats, food products including agricultural, meat, poultry and fish products, pharmaceutical products, cosmetic products, adhesives, paints and coatings (before and after applications. Even non-polymeric products which degrade by environmental conditions such as temperature, humidity, severe chemical environments, and mechanical stress conditions may be monitored by conductive composite sensors utilizing the methods of this disclosure. The degradable products monitored may be solids, liquids or gasses. The sensor elements may be solids, liquids or gasses.

Although the description above contains many specifications, these should not be construed as limiting the scope of the invention but merely providing illustrations of some of the presently preferred embodiments of this invention. Thus the scope of the invention should be determined by the appended claims and their legal equivalents, rather than by the examples given.

We claim:

1. A sensor element for detecting degradation of an environmentally sensitive product comprising:
    a plurality of electrically conductive particles and a control agent dispersed in a polymeric matrix;
    wherein said control agent is selected to influence a reaction rate of said sensor element to selected environmental conditions so that change of an electrical measurement of said sensor element is correlatable to said degradation of said environmentally sensitive product.

2. The sensor element of claim 1 wherein said control agent is selected to adjust a reaction rate of an environmentally dependent reaction of said sensor element correlatable to a selected degradation measurement of said environmentally sensitive product.

3. The sensor element of claim 1 wherein said control agent is selected to adjust an activation energy of an environmentally dependent reaction of said sensor element correlatable to a selected degradation measurement of said environmentally sensitive product.

4. The sensor element of claim 1 wherein said control agent is selected to adjust a time constant of an environmentally dependent reaction of said sensor element correlatable to a selected degradation measurement of said environmentally sensitive product.

5. The sensor element of claim 1 wherein said control agent is selected to adjust an activation energy and a time constant of an environmentally dependent reaction of said sensor element correlatable to a selected degradation measurement of said environmentally sensitive product.

6. The sensor element of claim 1 wherein said polymeric matrix comprises a thermoset and said control agent is a catalyst.

7. The sensor element of claim 1 wherein said polymeric matrix comprises a thermoset and said control agent is a hardener.

8. The sensor element of claim 1 wherein a temperature-dependent volatility of said control agent provides said change of an electrical property of said sensor element correlatable to said degradation of said environmentally sensitive product.

9. The sensor element of claim 8 wherein said temperature-dependent volatility of said control agent is higher than a temperature-dependent volatility of said polymeric matrix.

10. The sensor element of claim 1 wherein said control agent is selected to correlate a decrease of electrical resistivity of said sensor element to temperature-induced degradation of a temperature-sensitive product.

11. The sensor element of claim 1 wherein said degradation of said environmentally sensitive product is mechanical degradation.

12. The sensor element of claim 1 wherein said degradation of said environmentally sensitive product is chemical degradation.

13. The sensor element of claim 1 wherein said degradation of said environmentally sensitive product is biological degradation.

14. The sensor element of claim 1 wherein said environmentally sensitive product is a food product.

15. The sensor element of claim 1 wherein said environmentally sensitive product is a pharmaceutical product.

16. The sensor element of claim 1 wherein said environmentally sensitive product is a cosmetic product.

17. A method of detecting degradation of an environmentally sensitive product comprising the steps:
    taking a first electrical measurement of a conductive composite degradation sensor in communication with said environmentally sensitive product, said degradation sensor comprising a polymeric matrix, conductive filler particles and a control agent selected to affect the rate of an environmentally affected reaction of said degradation sensor; and
    correlating said first electrical measurement to a degraded state of said environmentally sensitive product, said correlating incorporating degradation data of previously degraded environmentally sensitive product portion and electrical property data of at least one previously degraded test sensor comprising said polymeric matrix, said conductive filler particles and said control agent.

18. The method of detecting degradation of claim 17 wherein said rate of an environmentally affected reaction is an activation energy of said reaction.

19. The method of detecting degradation of claim 17 wherein said rate of an environmentally affected reaction is a time constant of said reaction.

20. The method of detecting degradation of claim 17 wherein said correlating said first electrical measurement to a degraded state of said environmentally sensitive product incorporates at least one electrical property measurement of said test sensor in a first plurality of environmental conditions and at least one measurement of a degraded state of said environmentally sensitive product portion in a second plurality of environmental conditions.

21. The method of detecting degradation of claim 17 wherein said electrical property is electrical resistivity.

22. The method of claim 20 wherein said correlating said first electrical measurement to a degraded state of said environmentally sensitive product is performed by a reader capable of measuring electrical resistance by electrical communication with said sensor element.

* * * * *